(12) United States Patent
Parihar et al.

(10) Patent No.: US 10,639,029 B2
(45) Date of Patent: May 5, 2020

(54) SUTURE GRASPING INSTRUMENT

(71) Applicant: ETHICON LLC, Guaynabo, PR (US)

(72) Inventors: Shailendra K. Parihar, Mason, OH (US); Jason L. Harris, Lebanon, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 204 days.

(21) Appl. No.: 15/637,702

(22) Filed: Jun. 29, 2017

(65) Prior Publication Data

US 2019/0000440 A1  Jan. 3, 2019

(51) Int. Cl.
*A61B 17/04* (2006.01)
*A61B 17/06* (2006.01)
(Continued)

(52) U.S. Cl.
CPC ...... *A61B 17/0469* (2013.01); *A61B 17/0482* (2013.01); *A61B 17/0485* (2013.01); *A61B 17/06109* (2013.01); *A61B 17/3417* (2013.01); *A61B 17/3421* (2013.01); *A61B 17/0057* (2013.01); *A61B 17/0483* (2013.01); *A61B 2017/00349* (2013.01); *A61B 2017/00637* (2013.01); *A61B 2017/00663* (2013.01);
(Continued)

(58) Field of Classification Search
CPC ............ A61B 17/0469; A61B 17/0401; A61B 17/0482; A61B 17/00234; A61B 17/0485; A61B 17/06109; A61B 17/0057; A61B 17/0483; A61B 17/3417; A61B 17/3421; A61B 2017/06042; A61B 2017/00349; A61B 2017/0409; A61B 2017/0472; A61B 2017/0496; A61B 2017/06052; A61B 2017/0646; A61B 2017/00637; A61B 2017/00663; A61B 2017/06009; A61M 5/3291
See application file for complete search history.

(56) References Cited

U.S. PATENT DOCUMENTS 4,372,302 A * 2/1983 Akerlund ............... A61F 6/18
                                                    128/840
5,281,237 A * 1/1994 Gimpelson ........ A61B 17/0469
                                                    606/139
(Continued)

FOREIGN PATENT DOCUMENTS

WO    WO 2015/017547 A1    2/2015

OTHER PUBLICATIONS

U.S. Appl. No. 15/637,683, filed Jun. 29, 2017.
(Continued)

*Primary Examiner* — Ryan J. Severson
*Assistant Examiner* — Mohamed G Gabr
(74) *Attorney, Agent, or Firm* — Frost Brown Todd LLC

(57) ABSTRACT

A suture passer includes a needle extending longitudinally and configured to be manipulated between a catch position and a release position and a first suture notch and a second suture notch. The first and second suture notches extend respectively through the needle with a first catch undercut and a second catch undercut. Each of the first and second suture notches are configured to receive a suture thread therein and releasably capture the suture thread radially inwardly as the needle is manipulated toward the catch direction.

20 Claims, 13 Drawing Sheets

(51) Int. Cl.
*A61B 17/00* (2006.01)
*A61B 17/34* (2006.01)
*A61M 5/32* (2006.01)

(52) U.S. Cl.
CPC .............. *A61B 2017/06009* (2013.01); *A61B 2017/06042* (2013.01); *A61M 5/3291* (2013.01)

(56) References Cited

U.S. PATENT DOCUMENTS

| | | | |
|---|---|---|---|
| 5,792,135 | A | 8/1998 | Madhani et al. |
| 5,817,084 | A | 10/1998 | Jensen |
| 5,878,193 | A | 3/1999 | Wang et al. |
| 6,231,565 | B1 | 5/2001 | Tovey et al. |
| 6,364,888 | B1 | 4/2002 | Niemeyer et al. |
| 6,783,524 | B2 | 8/2004 | Anderson et al. |
| 7,524,320 | B2 | 4/2009 | Tierney et al. |
| 7,691,098 | B2 | 4/2010 | Wallace et al. |
| 7,806,891 | B2 | 10/2010 | Nowlin et al. |
| 7,981,092 | B2 | 7/2011 | Duke |
| 8,177,796 | B2 | 5/2012 | Akyuz et al. |
| 8,226,553 | B2 | 7/2012 | Shelton, IV et al. |
| 8,251,900 | B2 | 8/2012 | Ortiz et al. |
| 8,479,969 | B2 | 7/2013 | Shelton, IV |
| 8,568,362 | B2 | 10/2013 | Moreno et al. |
| 8,573,461 | B2 | 11/2013 | Shelton, IV et al. |
| 8,573,465 | B2 | 11/2013 | Shelton, IV |
| 8,579,807 | B2 | 11/2013 | Moreno et al. |
| 8,602,288 | B2 | 12/2013 | Shelton, IV et al. |
| 8,616,431 | B2 | 12/2013 | Timm et al. |
| 8,636,686 | B2 | 1/2014 | Minnelli et al. |
| 8,690,831 | B2 | 4/2014 | Duke |
| 8,783,541 | B2 | 7/2014 | Shelton, IV et al. |
| 8,800,838 | B2 | 8/2014 | Shelton, IV |
| 8,820,605 | B2 | 9/2014 | Shelton, IV |
| 8,844,789 | B2 | 9/2014 | Shelton, IV et al. |
| 9,301,759 | B2 | 4/2016 | Spivey et al. |
| 9,687,226 | B2 | 6/2017 | Hodgkinson et al. |
| 9,700,303 | B2 | 7/2017 | Prior et al. |
| 2006/0069399 | A1* | 3/2006 | Weisel ............... A61B 17/0483 606/148 |
| 2008/0200950 | A1 | 8/2008 | Wohlert |
| 2015/0038793 | A1 | 2/2015 | Prior et al. |
| 2015/0320417 | A1* | 11/2015 | Stewart ............... A61B 17/0469 606/144 |
| 2017/0281154 | A1 | 10/2017 | Hess et al. |

OTHER PUBLICATIONS

U.S. Appl. No. 15/637,688, filed Jun. 29, 2017.
U.S. Appl. No. 15/637,690, filed Jun. 29, 2017.
U.S. Appl. No. 15/637,696, filed Jun. 29, 2017.
U.S. Appl. No. 15/637,707, filed Jun. 29, 2017.
U.S. Appl. No. 15/637,712, filed Jun. 29, 2017.
U.S. Appl. No. 15/637,735, filed Jun. 29, 2017.
U.S. Appl. No. 15/637,778, filed Jun. 29, 2017.
European Search Report and Written Opinion dated Aug. 30, 2018 for Application No. EP 18180376.8, 8 pgs.
International Search Report and Written Opinion dated Aug. 30, 2018 for Application No. PCT/IB2018/054521, 13 pgs.

* cited by examiner

SUTURE GRASPING INSTRUMENT

BACKGROUND

Surgical procedures may require a clinician to gain access to a cavity or other desirable surgical site within a body of a patient. To perform such a surgical procedure, an incision may be made through a tissue of the patient into the cavity. Some conventional surgical procedures may apply a knife, such as a scalpel, to the tissue for the incision, while some less invasive surgical procedures, such as laparascopic and endoscopic surgical procedures, may access the cavity through a trocar assembly. Trocar assemblies generally include a trocar obturator received within a trocar cannula. In use, the clinician directs the trocar obturator and the cannula through the tissue in order to access the cavity of the desirable surgical site. Once accessed, the clinician withdraws the trocar obturator from the trocar cannula so that the trocar cannula may be used to introduce surgical instruments into the cavity for treatment.

Merely exemplary trocar assemblies, components thereof, and other varieties of wound closure devices are provided for in U.S. Pat. No. 7,981,092, entitled "Vibratory Trocar," issued Jul. 19, 2011; U.S. Pat. No. 8,226,553, entitled "Access Device with Insert," issued on Jul. 24, 2012; U.S. Pat. No. 8,251,900, entitled "Surgical Access Devices and Methods Providing Seal Movement in Predefined Paths," issued on Aug. 28, 2012; U.S. Pat. No. 8,579,807, entitled "Absorbing Fluids in a Surgical Access Device," issued on Nov. 12, 2013; U.S. Pat. No. 8,568,362, entitled "Surgical Access Device with Sorbents," issued on Oct. 29, 2013; U.S. Pat. No. 8,636,686, entitled "Surgical Access Device," issued on Jan. 28, 2014; U.S. Pat. No. 8,690,831, entitled "Gas Jet Fluid Removal in a Trocar," issued on Apr. 8, 2014; U.S. Pat. Pub. No. 2008/0200950, entitled "Surgical Hook," published on Aug. 21, 2008; now abandoned; U.S. Pat. Pub. No. 2015/0038793, entitled "Devices, Systems, and Methods for Providing Surgical Access and Facilitating Closure of Surgical Access Openings," published on Feb. 5, 2015, issued as U.S. Pat. No. 10,258,324 on Apr. 16, 2019; U.S. Pat Pub. No. 2015/0038994, entitled "Devices, Systems, and Methods for Providing Surgical Access and Facilitating Closure of Surgical Access Openings," published on Feb. 5, 2015, issued as U.S. Pat. No. 9,700,303 on Jul. 11, 2017; and U.S. Pat. Pub. No. 2015/0094741, entitled "Wound Closure Device including Mesh Barrier." Published on Apr. 2, 2015, issued U.S. Pat. No. 9,687,226 on Jun. 27, 2017. The disclosure of each of the above-cited U.S. patents and publications is incorporated by reference herein.

Surgical instruments for use with such trocars may have a distal end effector for engaging tissue through the trocar cannula in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Laparoscopic and endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the cavity of the patient. Positioning of an end effector may be further facilitated through inclusion of one or more articulation joints or features, enabling the end effector to be selectively articulated or otherwise deflected relative to the longitudinal axis of the shaft.

While various kinds of surgical instruments, including trocar assemblies and end effectors, and other associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
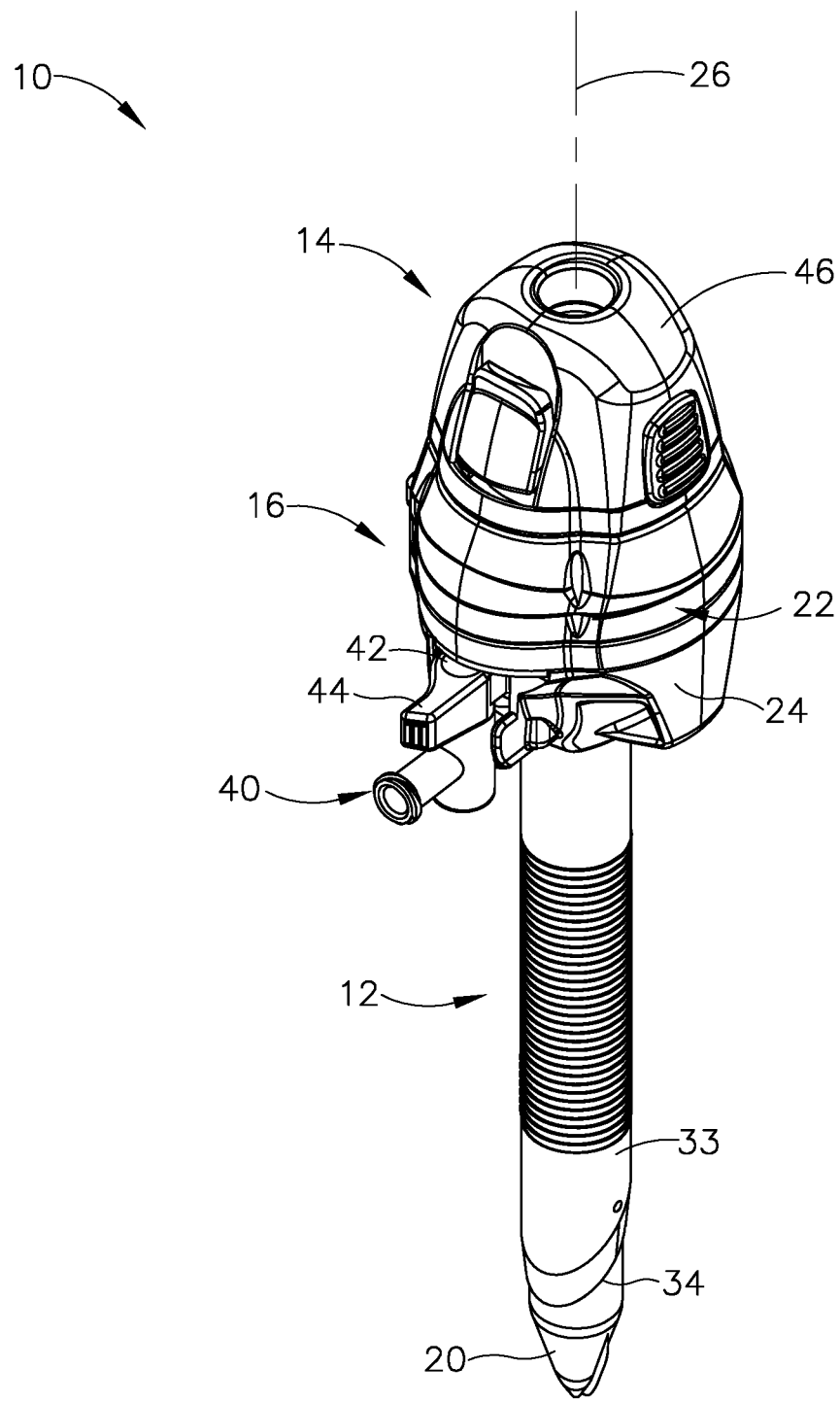
FIG. 1 depicts a perspective view of an exemplary trocar assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Access Device

Figure 2:
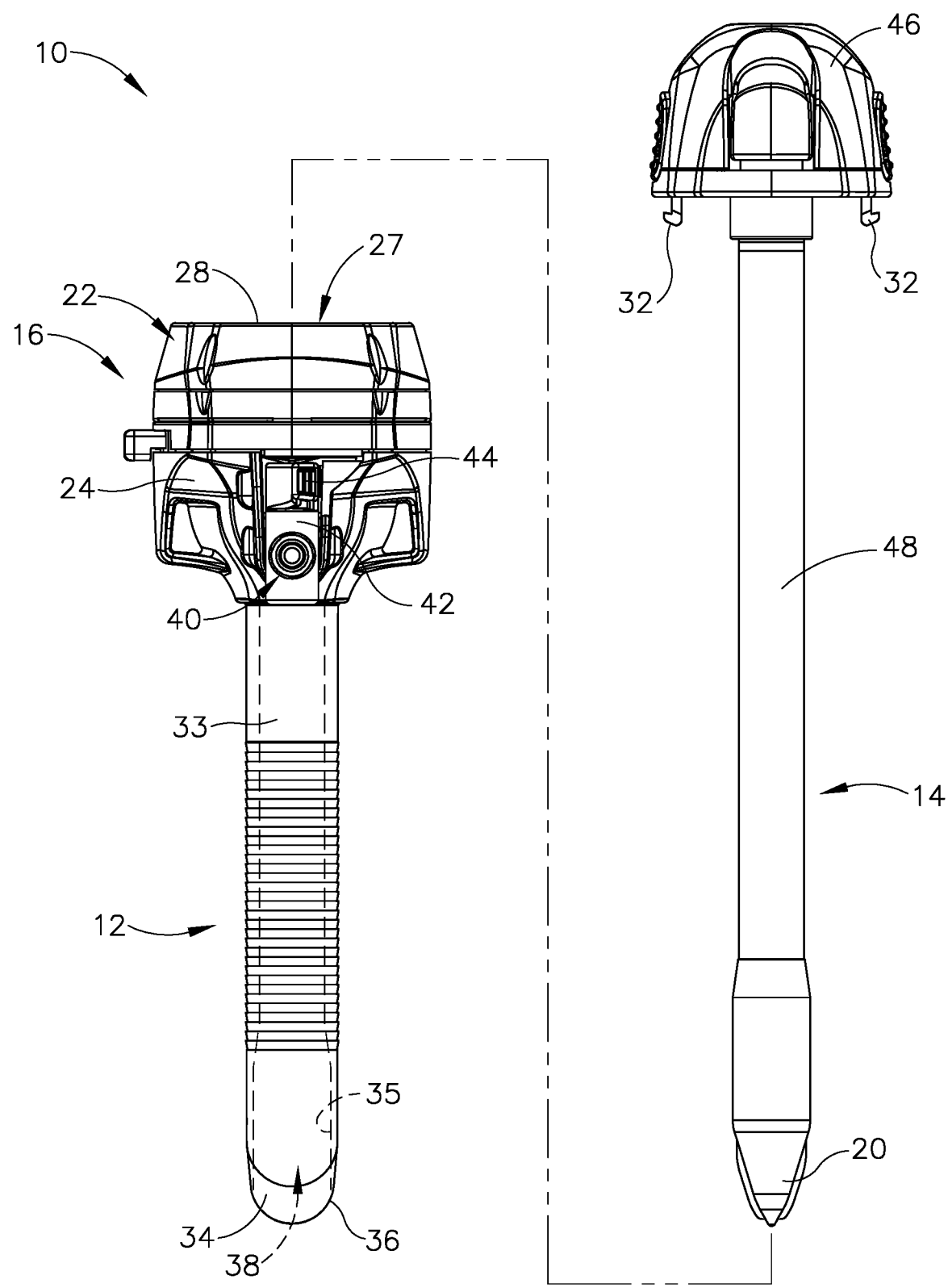
FIG. 2 depicts a partially exploded side elevational view of the trocar assembly of FIG. 1 having a trocar housing, a trocar cannula, and an obturator.

FIGS. 1-2 depict an exemplary surgical access device in the form of a first exemplary trocar assembly (10) that includes a trocar cannula (12) and a trocar obturator (14). Trocar obturator (14) is removably received within trocar cannula (12) through a trocar housing (16) of trocar cannula (12). As shown in FIG. 1 with trocar obturator (14) positioned within trocar cannula (12), a clinician inserts trocar assembly (12) through tissue (17) (see FIG. 3A) of a patient at a desirable surgical site for accessing a cavity (18) (see FIG. 3A) within the patient. By way of example only, trocar assembly (10) may be inserted in a patient's abdomen, between two of the patient's ribs, or elsewhere. A tip (20) of trocar obturator (14) projects distally from trocar cannula (12) to puncture tissue (17) (see FIG. 3A) for introducing a distal end portion of trocar cannula (12) into cavity (18) (see FIG. 3B). The clinician proximally withdraws trocar obturator (14) from trocar cannula (12) such that cavity (18) (see FIG. 3C) within the patient is in communication with a surgical environment via trocar cannula (12). The clinician may then introduce a fluid, such as a gas, through trocar cannula (12) for inflating cavity (18) (see FIG. 3A) and/or an end effector of a surgical instrument through trocar cannula (12) for engaging tissue (17) to achieve a diagnostic or therapeutic effect.

It should be understood that terms such as "proximal" and "distal" are used herein with reference to the clinician gripping trocar housing (16). Thus, tip (20) is distal with respect to the more proximal trocar housing (16). It will be further appreciated that for convenience and clarity, spatial terms such as "vertical" and "horizontal" are used herein with respect to the drawings. However, surgical instruments are used in many orientations and positions, and these terms are not intended to be limiting and absolute. Further, in some instances, components are referred to interchangeably with and without the term "assembly," e.g., a trocar and a trocar assembly. There is no particular intention for the terms to refer to different components. Likewise, terms such as "instrument" and "device" may be used interchangeably.

A. Exemplary Trocar Assembly with Cannula and Obturator

Trocar assembly (10) of FIGS. 1-2 includes cannula (12) extending distally from trocar housing (16). In the present example, trocar housing (16) has a generally cylindrical shape with a proximal removable cap (22) atop a distal housing chamber (not shown). Cap (22) is selectively attachable and detachable from housing chamber (not shown). Trocar housing (16) includes a housing sidewall (24) that extends circumferentially around a central longitudinal axis (26) through trocar assembly (10), and thus along trocar cannula (12). Trocar housing (16) further includes a central lumen (27) extending from a proximal housing end opening (28) to a distal housing end opening (not shown). As shown, cap (22) selectively mates with housing sidewall (24) via distal mating members (not shown) and further includes proximal mating members, such as slots (not shown), configured to removably connect to a pair of tabs (32), respectively, that extend distally from a portion of obturator (14). However, it will be appreciated that alternative structures and devices may also be removably connected to cap (22) during use.

Cannula (12) extends distally from trocar housing (16), and is also generally defined by a cannula sidewall (33) extending circumferentially around central longitudinal axis (26). Cannula sidewall (33) extends distally to a beveled end (34) such that cannula sidewall (33) and beveled end (34) are configured to be inserted through tissue (17) (see FIG. 3A) as discussed below in greater detail for accessing cavity (18) (see FIG. 3A). To this end, cannula (12) generally has a smaller diameter than trocar housing (16), which is configured to remain exterior of tissue (17) (see FIG. 3C). In addition, cannula (12) defines an interior lumen (35) with a proximal cannula end opening (not shown) and a distal cannula end opening (36), which extends through beveled end (34). In the present example, distal housing end opening (not shown) of trocar housing (16) fluidly connects to proximal cannula end opening (not shown) such that central lumen (27) of trocar housing (16) and interior lumen (35) of cannula (12) define a working channel (38). Working channel (38) thus extends from proximal housing end opening (28) to distal cannula end opening (36) and is configured to receive one or more surgical instruments therethrough for accessing cavity (18).

Furthermore, an insufflation port (40) is operatively connected to trocar housing (16) to control the flow of an insufflation fluid, such as carbon dioxide, through a portion of cannula (12) and into cavity (18). More particularly, insufflation port (40) includes a stopcock valve (42) and a cock valve lever (44), which can work together to allow and/or prevent passage of the insufflation fluid into tubing (not shown), through trocar housing (16), and into trocar cannula (12). Trocar housing (16) and cannula (12) respectively have proximal and distal seal assemblies (not shown) positioned within central lumen (27) and interior lumen (35) of working channel (38). In the present example, the proximal seal assembly is an instrument seal (not shown), whereas the distal seal assembly (not shown) is a zero-closure seal, such as a duckbill seal (not shown). Instrument seal (not shown) is retained with cap (22) and configured to fluidly seal against a surgical instrument extending through working channel (38). In contrast, duckbill seal (not shown) is configured to form a seal in working channel (38) when no instrument is disposed therethrough to thereby inhibit the leakage of insufflation fluid during use. Of course, it will be appreciated that alternative seal assemblies may be positioned within working channel (38) for inhibiting such leakage of insufflation fluid.

As discussed briefly above, obturator (14) is used in conjunction with cannula (12) for inserting trocar assembly (10) into the patient. Obturator (14) of the present example, includes a handle head (46) with a cylindrical shaft (48) extending distally therefrom to tip (20), which is generally configured to puncture tissue (17) (see FIG. 3A) as described below in greater detail. Handle head (46) is configured to be gripped by the clinician during use and includes selectively movable tabs (32) extending distally to removably connect with trocar housing (16) for selective securement. Shaft (48) is received through working channel (38) such that tip (20) extends distally from beveled end (34). Of course, obturator (14) may be selectively removed from cannula (12) and trocar housing (16) to free working channel (38) for use. While the present example of trocar assembly (10) has obturator (14), it will be appreciated that cannula (12) may be inserted in some examples without obturator (14) or may be alternatively configured to aid insertion without using obturator (14).

B. Exemplary Method of Accessing a Cavity within a Patient

Figure 3A:
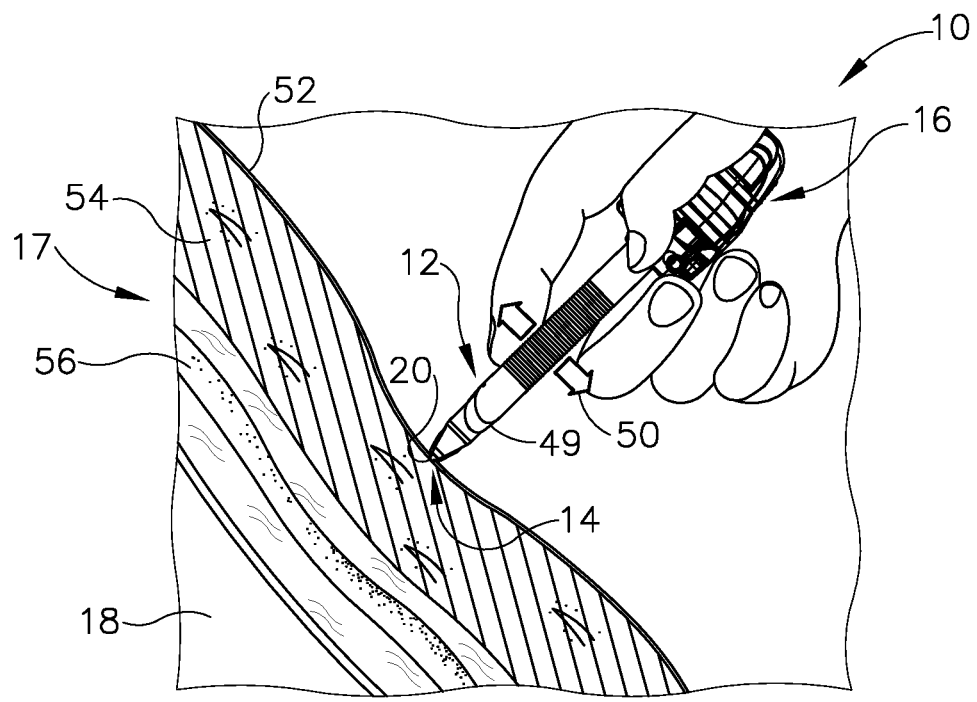
FIG. 3A depicts a sectional side view of tissue of a patient with the trocar assembly of FIG. 1 being manipulated by a clinician through the tissue.
Figure 3B:
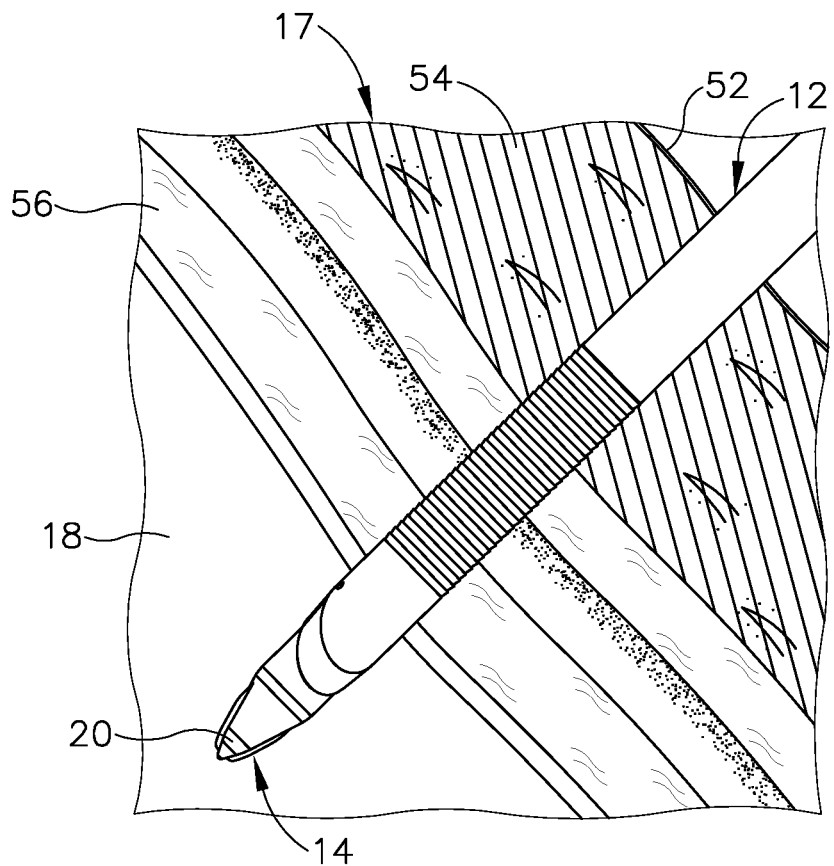
FIG. 3B depicts a sectional side view of the tissue and trocar assembly of FIG. 3A, with the trocar assembly of FIG. 1 inserted through the tissue and received within a cavity of the patient.
Figure 3C:
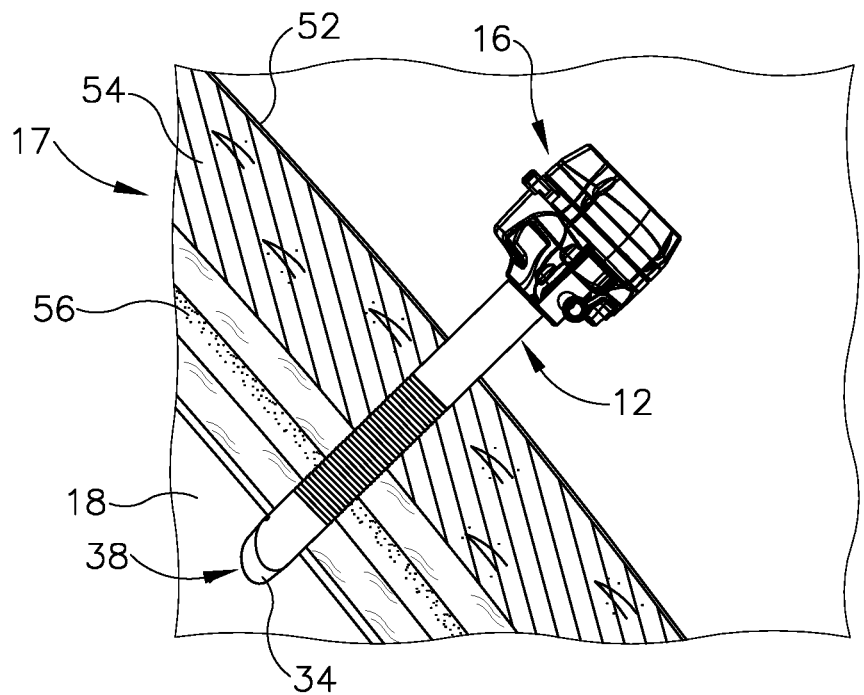
FIG. 3C depicts a sectional side view of the tissue and the trocar assembly of FIG. 3A, with the obturator withdrawn from the trocar cannula for accessing the cavity via a working channel through the trocar cannula and the trocar housing.
Figure 3D:
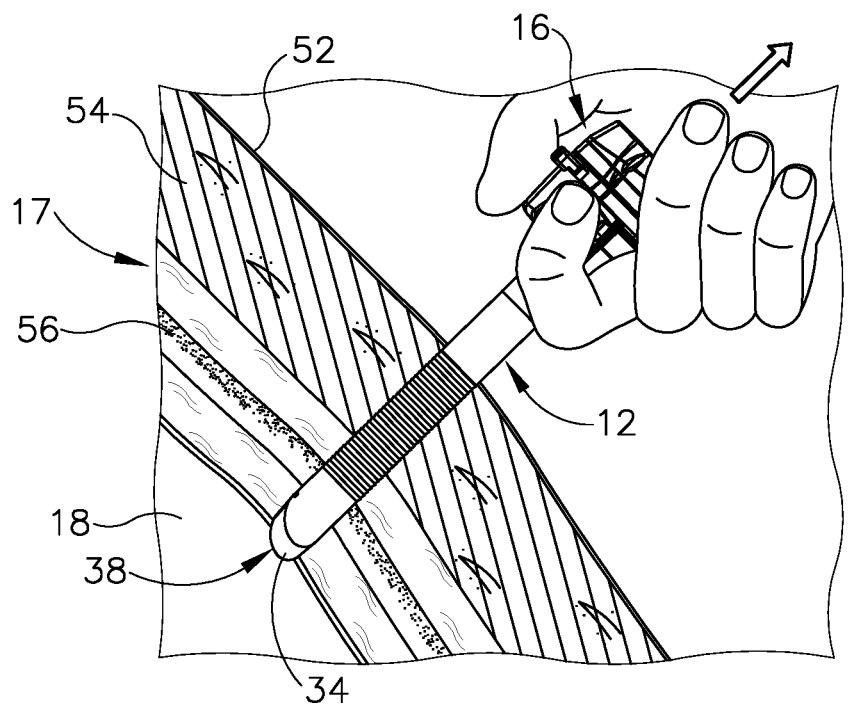
FIG. 3D depicts a sectional side view of the tissue and the trocar assembly of FIG. 3C, with the trocar housing and the trocar cannula being removed from the cavity and the tissue of the patient.

FIGS. 3A-3D illustrate accessing cavity (18) through tissue (17) with trocar assembly (10) discussed above. Tissue (17) of the present example more particularly has relatively outward superficial layers and relatively inward deep layers. Superficial layers generally include an outer layer of skin (52) and an inner layer of fat (54); whereas the deeper layers include layers of fascia (56), which are fibrous and flexible with relatively higher tensile strength than the superficial layers. As shown in FIG. 3A, with obturator (14) received within cannula (12) and connected to trocar housing (16), the clinician manipulates trocar assembly (10) to urge tip (20) of obturator (14) against skin (52) and inwardly toward cavity (18) while rotating trocar assembly (10) back and forth. Arrow (49) and arrow (50) respectively indicate this inward and rotatable movement. Continued inward urging of trocar assembly (10) further directs tip (20) and beveled end (34) of cannula (12) through the layers of fat (54) and fascia (56) and into cavity (18) as shown in FIG. 3B. The clinician then disconnects obturator (14) from trocar housing (16) and withdraws obturator (14) from cannula (12) to establish access from the exterior of tissue (17) into cavity (18) via working channel (38) as shown in FIG. 3C for achieving a diagnostic or therapeutic effect with another surgical instrument (not shown). Once the diagnostic or therapeutic effect is complete, clinician withdraws cannula (12) and trocar housing (16) outwardly for removal from tissue (17) as shown in FIG. 3D.

Figure 4A:
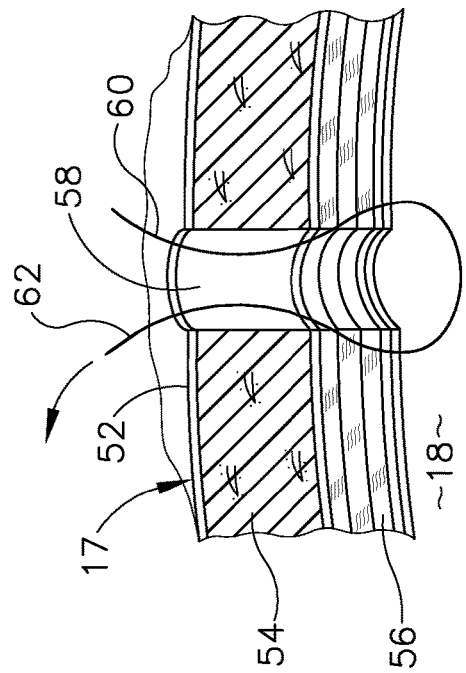
FIG. 4A depicts another sectional side view of the tissue shown in FIGS. 3A-3D following removal of the trocar assembly of FIG. 1, with an opening through the tissue and a suture thread being introduced into a portion of the tissue for suturing the opening closed.
Figure 4B:
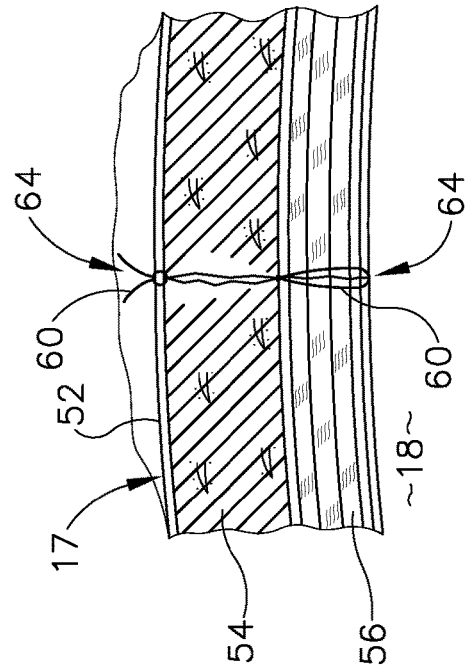
FIG. 4B depicts a sectional side view of the tissue of FIG. 4A, with the suture thread being introduced though another portion of the tissue and pulled through the tissue.
Figure 4C:
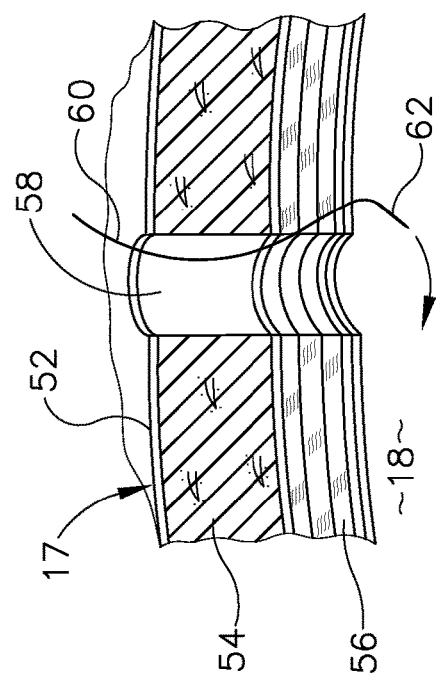
FIG. 4C depicts a sectional side view of the tissue of FIG. 4A, with the suture thread tightened and knotted for at least partially closing the opening.
Figure 4D:
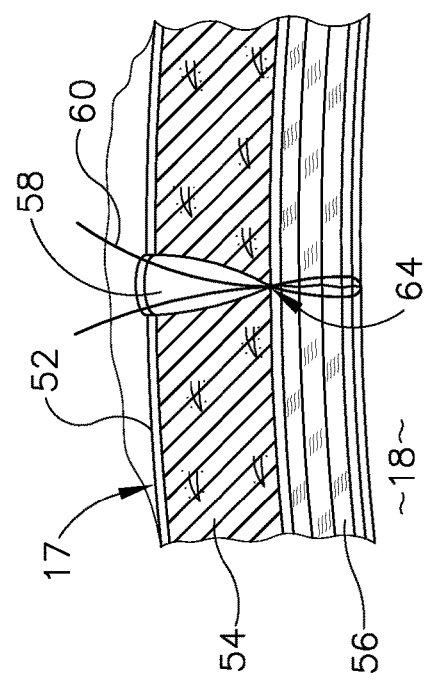
FIG. 4D depicts a sectional side view of the tissue of FIG. 4A, with additional suturing for further closing the opening.

As shown in FIG. 4A, removal of cannula (12) from tissue (17) generally results in a tissue opening (58), which may also be referred to as a tissue port or tissue wound, that clinician closes to encourage healing of tissue (17). While some tissue openings may sufficiently close as tissue (17) comes together, other openings, such as tissue opening (58), are sutured closed with a suture thread (60). In one example shown in FIGS. 4A-4D, suture thread (60) is removably coupled with a needle (62) for guiding suture thread (62) through tissue (17) as the clinician manipulates needle (62). More particularly, as shown in FIG. 4B, the clinician directs needle (62) downwardly through fascia (56) on one side of tissue opening (58) and then upwardly through fascia (56) on the other side of tissue opening (58) as needle (62) clears tissue (17). Notably, the clinician threads needle (62) though fascia (56) a desirable distance from tissue opening (58) in order to provide a relatively close proximity to tissue opening (58); but also at a sufficient distance to provide ample fascia (56) for anchoring suture thread (60) therein. As shown in FIG. 4C, suture thread (60) from respective sides of tissue opening (58) are brought together and pulled to similarly pull tissue (17) together and at least partially close tissue opening (58). The clinician then knots suture thread (60) to secure tissue (17) together and sufficiently close tissue opening (58) with a formed suture (64) as shown in FIG. 4D. Additional sutures (64) may be placed along tissue (17) to further close tissue opening (58) and encourage healing of tissue (17).

While the above described suturing technique shown in FIGS. 4A-4D is one exemplary procedure for closing tissue opening (58) with suture thread (60) following use of trocar assembly (10) (see FIG. 1), other exemplary procedures and devices may be alternatively used for closing such tissue openings. By way of example, U.S. patent application Ser. No. 15/088,723, entitled "Surgical Access Devices with Integrated Wound Closure Features," filed on Apr. 1, 2016, issued as U.S. Pat. No. 10,299,785 on May 28, 2019, which is incorporated by reference herein in its entirety, describes an alternative trocar assembly and suturing technique. To this end, alternative trocar assemblies and suturing techniques may be used in any combination as desired by the clinician.

II. Exemplary Suture Passer

Figure 5:
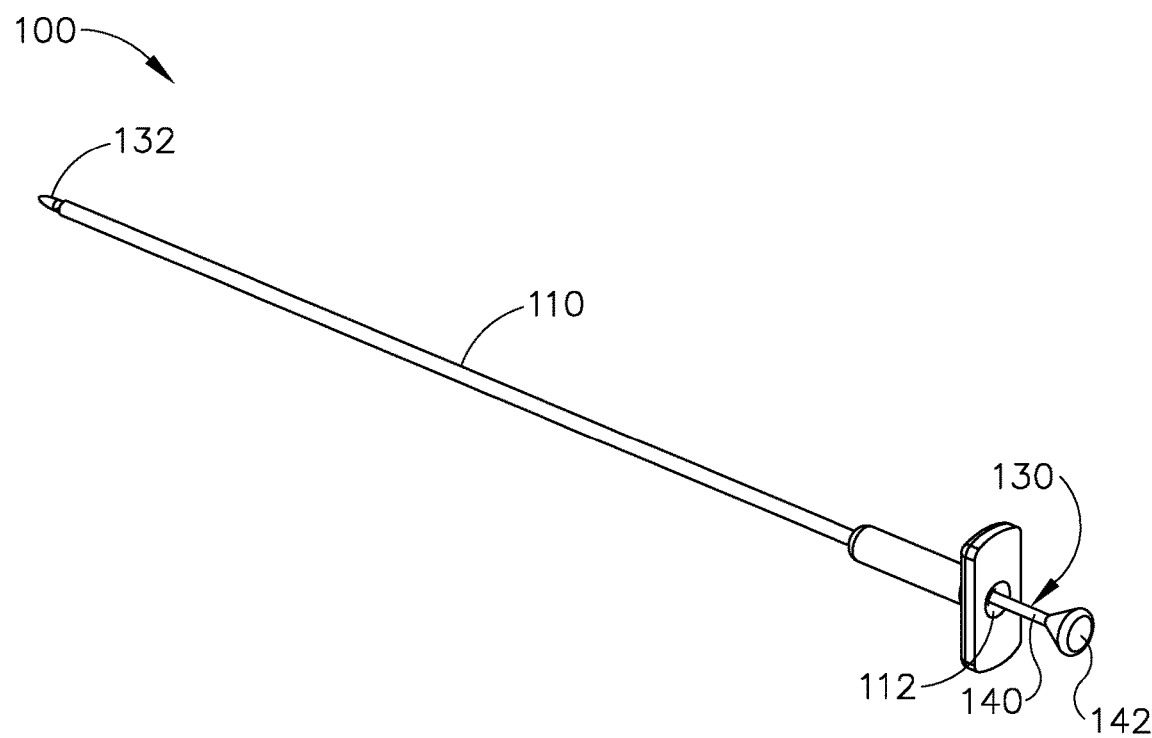
FIG. 5 depicts a perspective view of an exemplary suture passer having a first needle head.

Gripping suture thread (60) to manipulate suture thread (60) for closing tissue opening (58) may be difficult in some instances, particularly given limited access within tissue opening (58) and the relatively small size of suture thread (60). It may be thus beneficial to use a suture passer, such as a suture passer (100) as shown in FIG. 5, that is configured to catch and release suture thread (60) to facilitate closure of tissue opening (58) following removal of trocar assembly (10). For example, after suture thread (60) has been inserted through fascia (56) on one side of tissue opening (58), suture passer (100) catches suture thread (60) to facilitate redirection and selective repositioning of suture thread (60) upward toward fascia (56) on the other side of tissue opening (58) as discussed below in greater detail.

The following description provides various examples of suture passer (100) with various needle heads (132, 232, 332, 432) in FIGS. 5-15C configured to catch and securely hold suture thread (60) within a patient. Each needle head (132, 232, 332, 432) is configured to enable catching and releasing suture thread (60). Furthermore, suture passer (100) also includes various actuation mechanisms for covering and uncovering needle heads (132, 232, 332, 432) in use. Suture passer (100) and needle heads (132, 232, 332, 432) described below may be used with any of the various trocar assemblies (10) described above and in any of the various procedures described in the various references described herein. While the following examples are provided in the context of trocar assembly (10) described above, the teachings below may be readily incorporated into any other surgical access devices and instruments. Other suitable ways in which the below-described suture passer (100) may be used will be apparent to those of ordinary skill in the art in view of the teachings herein.

A. Exemplary Suture Passer with Biasing Member

Figure 6:
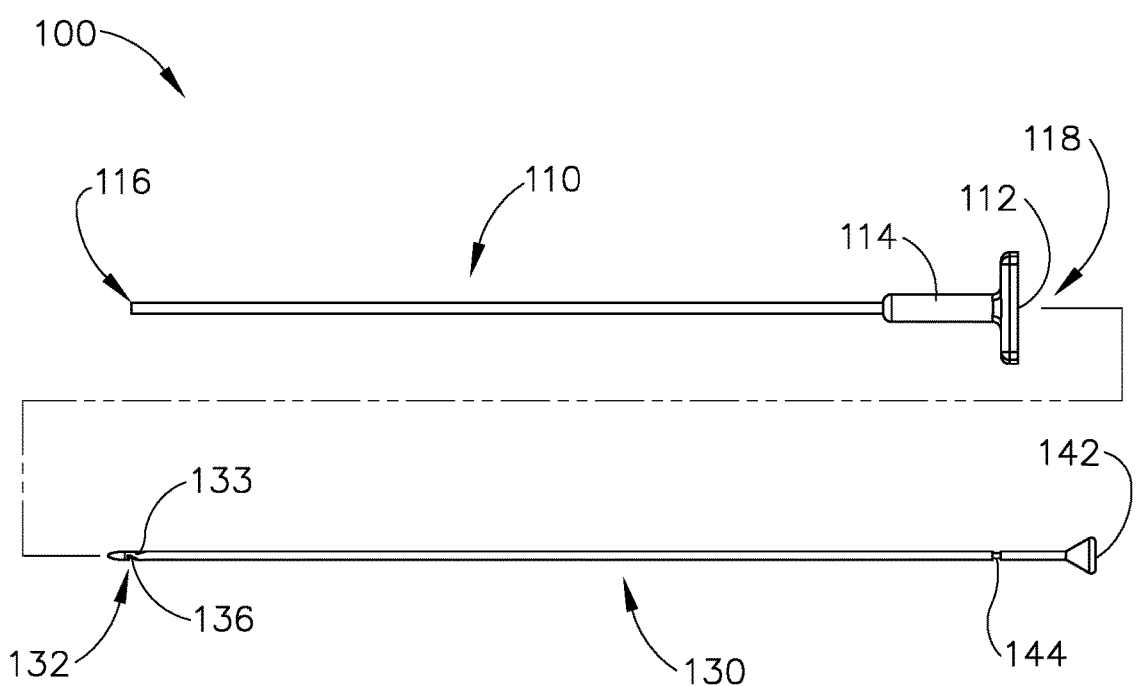
FIG. 6 depicts a partially exploded side elevational view of the suture passer of FIG. 5.

As shown in FIGS. 5-6, an exemplary suture passer (100) includes an outer sheath (110) and an inner needle (130). Inner needle (130) is substantially enclosed within outer sheath (110) such that the longitudinal length of inner needle (130) extends within a bore (112) of outer sheath (110). Inner needle (130) comprises a first needle head (132), a longitudinal shaft (140), and a driver (142). Longitudinal shaft (140) has a longitudinal length that separates needle head (132), positioned on a distal end of longitudinal shaft (140), from driver (142), positioned on an opposite, proximal end of longitudinal shaft (140). Needle head (132) of inner needle (130) comprises a proximal notch (133) and a distal notch (136). Outer sheath (110) comprises bore (112), a housing (114), a radial wall (115) (see FIG. 8) with a distal opening (116) (see FIG. 7A), and a proximal opening (118) (see FIG. 7A). Bore (112) has a longitudinal length that separates distal opening (116) (see FIG. 7A) from housing (114) and proximal opening (118) (see FIG. 7A). Openings (116, 118) (see FIG. 7A) are in communication with bore (112) and in axial alignment with the longitudinal length of bore (112). Inner needle (130) inserts into outer sheath (110) by directing needle head (132) into proximal opening (118) and slidably advancing inner needle (130) through bore (112). As further seen in FIG. 6, inner needle (130) further comprises a latch (144) configured to engage a biasing member (120) of outer sheath (110) and contained within housing (114).

As a merely illustrative example, inner needle (130) is formed of a hardened stainless steel while the molded features on inner needle (130), particularly driver (142) and latch (144), are formed of plastic, such as polycarbonate. Notches (133, 136) are machined into inner needle (130) in the present example, but may alternatively be molded with inner needle (130), such as by injection molding. In another example, inner needle (130) may be form of a plastic material and metal coated for additional surface hardness similar to stainless steel with a bending strength similar to aluminum. Inner needle (130) has a diameter smaller than a diameter of outer sheath (110) such that inner needle (130) is slidably received within outer sheath (110). For example, inner needle (130) has a diameter ranging from approximately 2 millimeters to approximately 3 millimeters and outer sheath (110) has a corresponding larger diameter with ample clearance configured to receive a United States Pharmacopeia (U.S.P.) designation 2 sized suture thread (60). Furthermore, outer sheath (110) is formed of a seamless stainless steel tubing. As will be apparent to those of ordinary skill in the art, outer sheath (110) and inner needle (130) may be formed of other, various suitable materials that will maintain durability when inserted into the cavity of a patient.

Figure 7A:
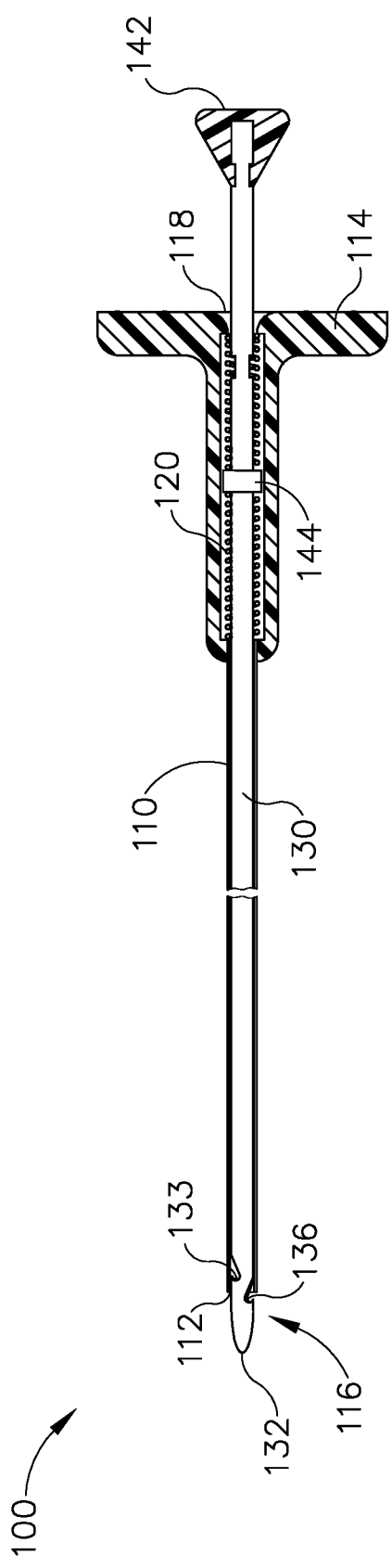
FIG. 7A depicts a cross-sectional side view of the suture passer of FIG. 5 taken along a centerline thereof with the needle in a retracted position and the biasing member in an expanded state.
Figure 7B:
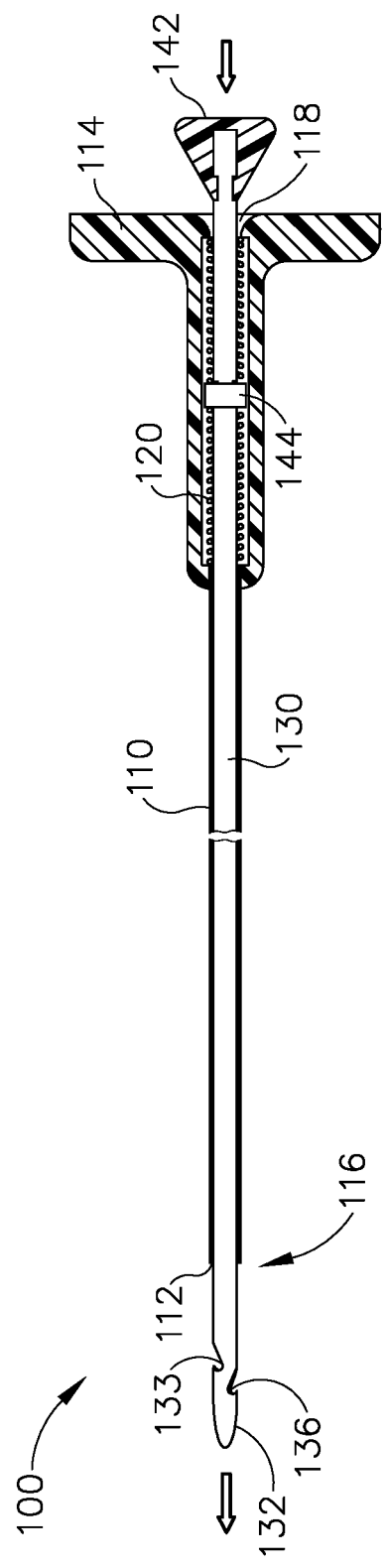
FIG. 7B depicts the cross-sectional side view of the suture passer similar to FIG. 7A, but with the needle in an extended position and the biasing member in a compressed state.

FIGS. 7A-7B show suture passer (100) transitioning respectively from a retracted position to an extended position when a clinician exerts a distal force on driver (142). In particular, FIG. 7A illustrates suture passer (100) in the initial, retracted position where inner needle (130) is slidably inserted into bore (112) of outer sheath (110). Due to the natural expanded state of biasing member (120) being captured in compression, suture passer (100) generally remains in the retracted position unless manipulated toward the extended position by the clinician. While in the retracted position, needle head (132) of inner needle (130) is substantially contained within bore (112) at distal opening (116). Furthermore, proximal notch (133) and distal notch (136) are fully covered within bore (112) by outer sheath (110) in the retracted position, and driver (142) is fully extended from proximal opening (118). With suture passer (100) in the retracted position, the potential for notches (133, 136) to contact tissue opening (58) or other portion of the patient's body in use is reduced as notches (133, 136) remain covered within outer sheath (110). Biasing member (120) within housing (114) is similarly in a fully extended state and securely engaged with latch (144) of inner needle (130). Latch (144) is configured to movably secure inner needle (130) to outer sheath (110) such that inner needle (130) has limited translational movement that does not distally slide out of outer sheath (110) from distal opening (116).

In the present example, the clinician grasps suture passer (100) at housing (114) to selectively position needle head (132) adjacent to suture thread (60) (see FIG. 4A) within a cavity of the patient. Upon exertion by the clinician on driver (142) of the predetermined force to overcome the resilient bias created by biasing member (120), inner needle (130) slidably translates within bore (112) in the distal direction, as seen in FIG. 7B. Biasing member (120) compresses to a compressed state while suture passer (100) is in the extended position and driver (142) is held distally towards housing (114). As a merely illustrative example, biasing member (120) has a spring rate ranging from approximately 2.3 lbs./inch to approximately 2.8 lbs./inch, although other spring rates configured to provide for a relatively smooth translation of inner needle (130) within outer sheath (110) may be similarly used. With suture passer (100) in the extended position, needle head (132) of inner needle (130) extends distally through distal opening (116) such that notches (133, 136) extend beyond bore (112) of outer sheath (110). In this instance, inner needle (130) and notches (133, 136) are configured to be physically maneuvered within tissue opening (58) to catch and subsequently release suture thread (60) (see FIG. 4A).

Figure 8:
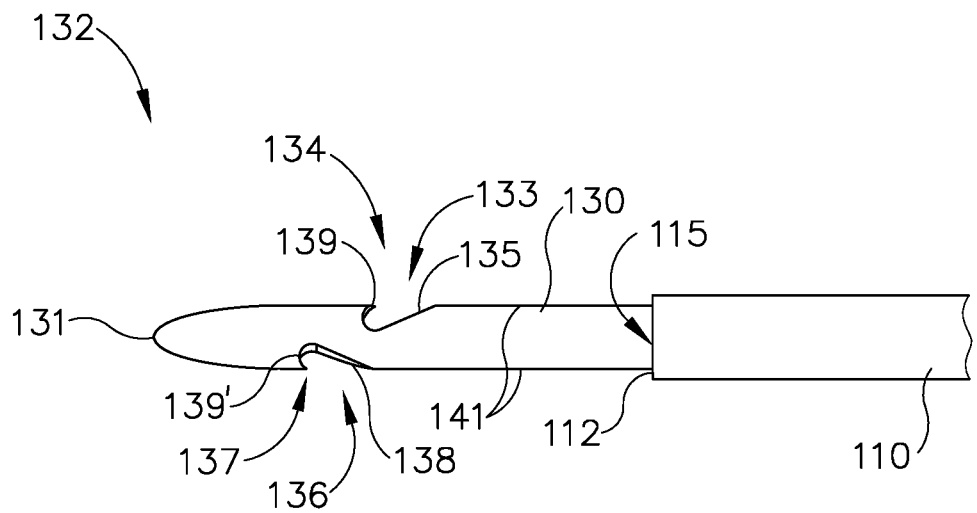
FIG. 8 depicts a side elevational view of the first needle head of the suture passer of FIG. 5.

FIG. 8 shows needle head (132) of inner needle (130) exposed beyond bore (112) of outer sheath (110) when suture passer (100) is in the extended position. In addition to notches (133, 136), needle head (132) further comprises a domed pointer (131) geometrically configured to provide inner needle (130) with a smooth, low force impact when inner needle (130) is inserted into tissue opening (58) (see FIG. 4A). With this unsharpened point, domed pointer (131) is configured to inhibit inadvertent damage to tissue when inserting suture passer (100) within the patient.

Proximal notch (133) extends through inner needle (130) and comprises a proximal catch undercut (134) and a proximal release cam surface (135). Proximal catch undercut (134) has a hooked surface (139) and is configured to receive and hold suture thread (60) (see FIG. 4A) radially inwardly toward inner needle (130) when inner needle (130) is selectively maneuvered to catch suture thread (60) (see FIG. 4A). Proximal release cam surface (135) is positioned between proximal catch undercut (134) and an outer radial surface (141) of inner needle (130). Proximal release cam surface (135) extends proximally and radially outwardly from hooked surface (139) of proximal catch undercut (134) until flush with outer radial surface (141) of inner needle (130). Proximal release cam surface (135) is configured to urge suture thread (60) (see FIG. 4A) radially outwardly from proximal catch undercut (134) to thereby remove suture thread (60) (see FIG. 4A) from proximal notch (133) when inner needle (130) is selectively maneuvered to release suture thread (60) (see FIG. 4A).

Similarly, distal notch (136) extends through inner needle (130) and comprises a distal catch undercut (137) and a distal release cam surface (138). Distal catch undercut (137) has a hooked surface (139') and is configured to receive and hold suture thread (60) (see FIG. 4A) radially inwardly towards inner needle (130) when inner needle (130) is selectively maneuvered in a catch direction to catch suture thread (60) (see FIG. 4A). Distal release cam surface (138) is positioned between distal catch undercut (137) and outer radial surface (141) of inner needle (130). Distal release cam surface (138) extends distally and radially outwardly from hooked surface (139') of distal catch undercut (137) until becoming level with outer radial surface (141) of inner needle (130). Distal release cam surface (138) is configured to urge suture thread (60) (see FIG. 4A) radially outwardly from distal catch undercut (137) to thereby remove suture thread (60) (see FIG. 4A) from distal notch (136) when inner needle (130) is selectively maneuvered in a release direction to release suture thread (60) (see FIG. 4A).

As best seen in FIG. 8, notches (133, 136) are positioned along inner needle (130) at varying angular positions about a longitudinal axis (129) such that proximal notch (133) is angularly positioned on inner needle (130) opposite of distal notch (136). Notwithstanding the relative positioning of notches (133, 136) relative to each other along inner needle (130), catch undercuts (134, 137) are distally oriented on inner needle (130) relative to release cam surfaces (135, 138), respectively. Although not shown, it should be understood that proximal notch (133) and/or distal notch (136) may be orientated along inner needle (130) in an opposite position than that depicted in FIG. 8. In this instance, catch undercuts (134, 137) are proximally oriented on inner needle (130) relative to release cam surfaces (135, 138), respectively.

Figure 9:
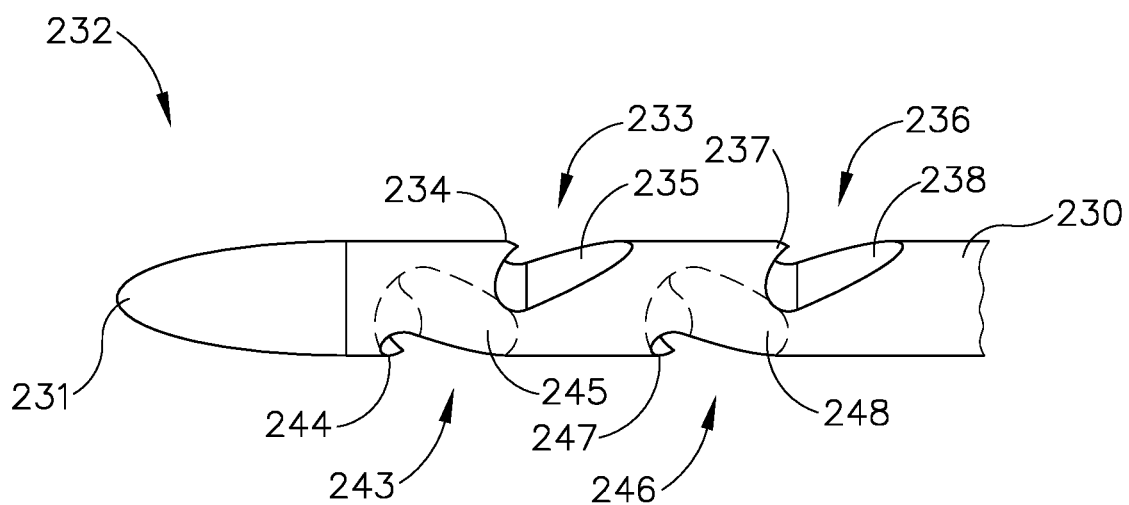
FIG. 9 depicts a side elevational view of a second needle head.

FIG. 9 depicts a second needle head (232) of an inner needle (230). Needle head (232) comprises first-side notches (233, 236), second-side notches (243, 246), and a domed pointer (231). Like domed pointer (131) (see FIG. 7A), domed pointer (231) is geometrically configured to provide inner needle (230) with a smooth, low force impact when inner needle (230) is inserted into tissue opening (58) (see FIG. 4A) to reduce the likelihood of damaging the tissue upon insertion of suture passer (100) into the patient. First-side notches (233, 236) extend through inner needle (230) and are positioned angularly opposite from second-side notches (243, 246) about a longitudinal axis (229) of inner needle (230). Like notches (133, 136) (see FIG. 7A) of inner needle (130) (see FIG. 7A), first-side notches (233, 236) and second-side notches (243, 246) respectively include catch undercuts (234, 237, 244, 247) and release cam surfaces (235, 238, 245, 248) configured to similarly perform as described above with respect to catch undercuts (134, 137) (see FIG. 7A) and release cam surfaces (135, 138) (see FIG. 7A).

Figure 10:
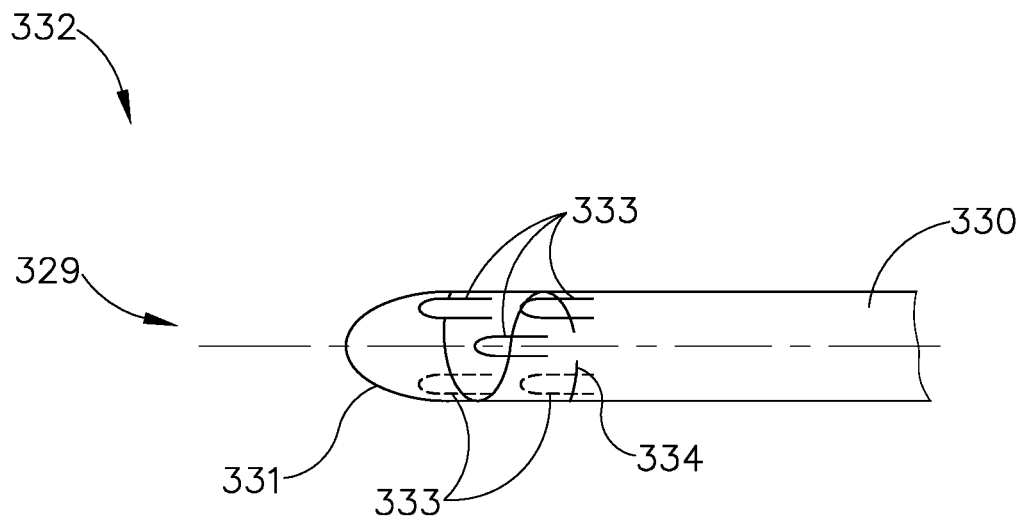
FIG. 10 depicts a side elevational view of a third needle head of the suture passer of FIG. 5.
Figure 11:
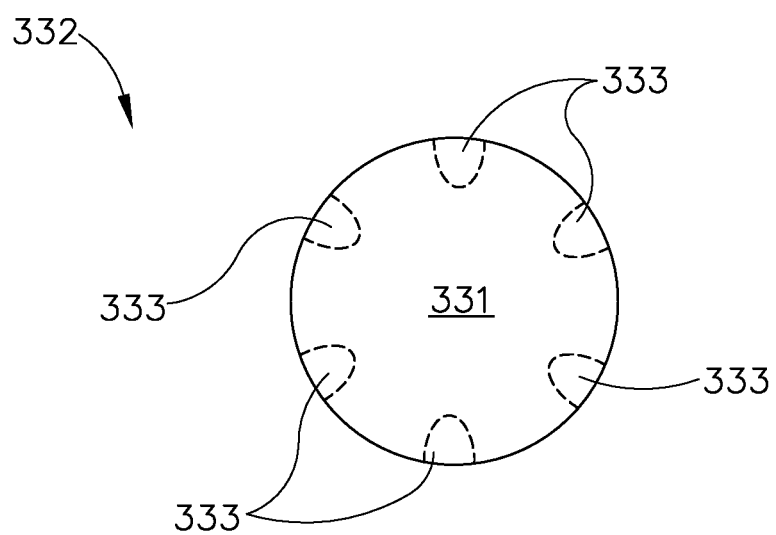
FIG. 11 depicts a distal end view of the needle head of FIG. 10.

FIGS. 10-11 illustrate a third needle head (332) of an inner needle (330). In the present example, needle head (332) comprises a plurality of notches (333) along inner needle (330) and a domed pointer (331). Plurality of notches (333) are angularly positioned along needle head (332) about a longitudinal axis (329) of inner needle (330) in a helical arrangement, as indicated by reference numeral (334). Although six notches (333) are depicted, it will be apparent to those of ordinary skill in the art that more or fewer notches (333) may be positioned along needle head (332).

B. Exemplary Suture Passer with Rotation Member

Figure 12:
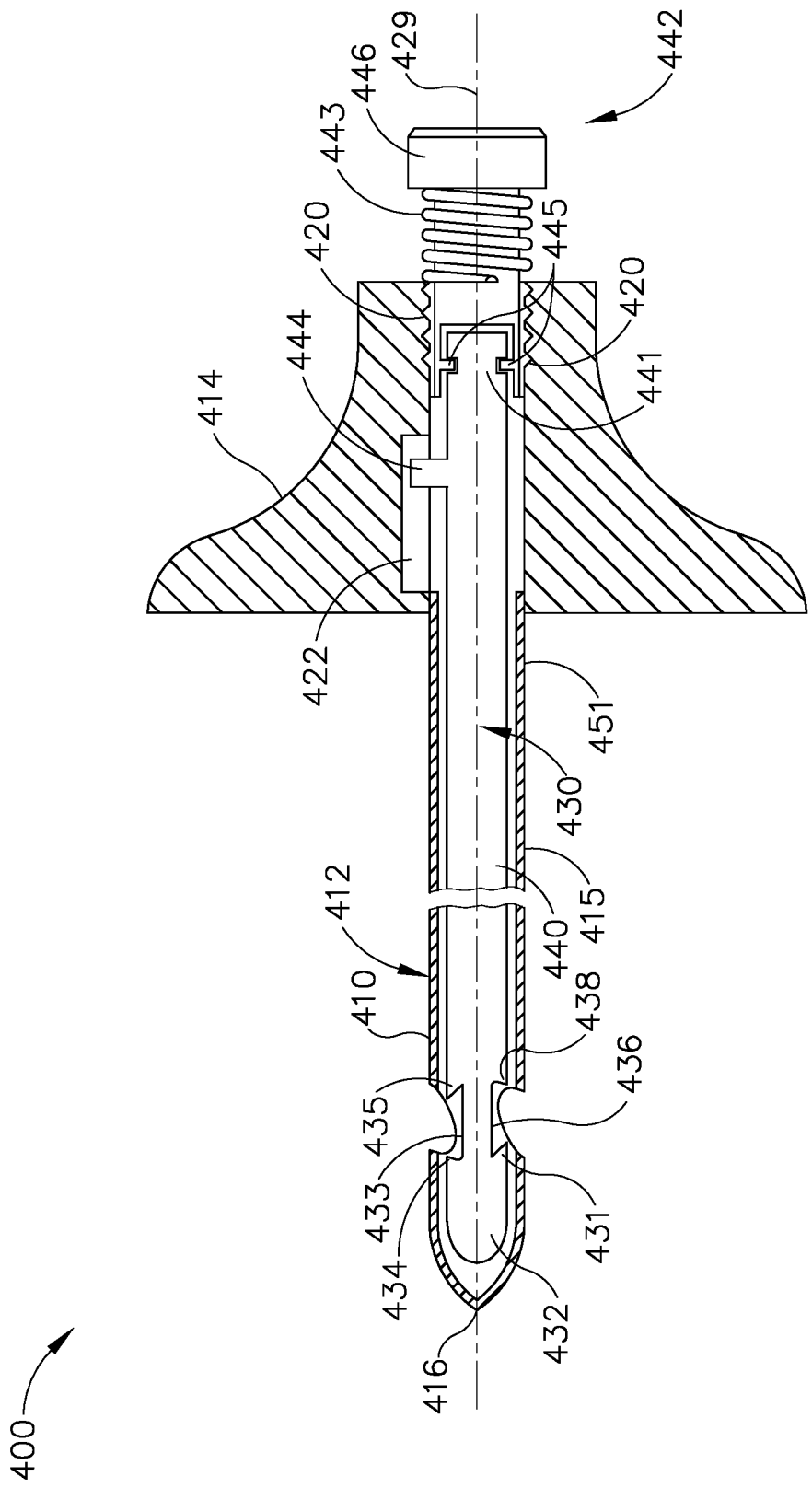
FIG. 12 depicts a cross-sectional side view of another exemplary suture passer with a rotating driver and a fourth needle head.

FIG. 12 depicts another exemplary suture passer (400) comprising an outer sheath (410) and an inner needle (430) with a fourth needle head (432). Inner needle (430) is substantially enclosed within outer sheath (410) such that the longitudinal length of inner needle (430) extends within a bore (412) of outer sheath (410). Inner needle (430) comprises needle head (432), a longitudinal shaft (440), and a driver (442). Longitudinal shaft (440) has a longitudinal length that separates needle head (432), positioned on a distal end of longitudinal shaft (440), from driver (442), positioned on an opposite, proximal end of longitudinal shaft (440). Driver (442) includes a knob (446), an external threaded portion (443), and an engagement mechanism (445). Longitudinal shaft (440) further includes an engagement coupling (441) configured to movably attach inner needle (430) to driver (442) by mating with the corresponding engagement mechanism (445) of driver (442).

Needle head (432) of inner needle (430) has an upper notch (433) and a lower notch (436) positioned angularly opposite of each other along inner needle (430). Upper notch (433) comprises an upper curved surface (434) and an upper hooked surface (435). Upper surfaces (434, 435) are positioned longitudinally opposite each other such that upper surfaces (434, 435) face each other along inner needle (430). Upper curved surface (434) is positioned distally relative to upper hooked surface (435). As will be described in greater detail below, upper curved surface (434) is configured to direct suture thread (60) (see FIG. 14A) toward an upper release cam surface (455) (see FIG. 13A) such that upper curved surface (434) pushes suture thread (60) (see FIG. 14A) out of upper notch (433), whereas upper hooked surface (435) is configured to catch and hold suture thread (60) (see FIG. 14A) against an upper catch undercut (454) (see FIG. 13A). Similarly, lower notch (436) comprises a lower hooked surface (437) and a lower curved surface (438). Lower surfaces (437, 438) are positioned longitudinally opposite each other such that lower surfaces (437, 438) face each other along inner needle (430). Lower hooked surface (437) is positioned distally relative to lower curved surface (438). As will be further described below, lower curved surface (438) is configured to direct suture thread (60) (see FIG. 15A) towards a lower release cam surface (458) (see FIG. 13A) such that lower curved surface (438) pushes suture thread (60) (see FIG. 15A) out of lower notch (436), whereas lower hooked surface (437) is configured to catch and hold suture thread (60) (see FIG. 15A) against a lower catch undercut (457) (see FIG. 13A). Although not shown, it should be understood that needle head (432) may comprise more or fewer notches (433, 436) along inner needle (430) than that depicted.

Outer sheath (410) comprises bore (412), a housing (414), a radial wall (415), and a distal end (416). Distal end (416) is angular with a cutting edge configured to pierce tissue (17). Bore (412) has a longitudinal length that separates distal end (416) from housing (414), which is positioned on a proximal end thereof. Inner needle (430) is configured to slidably translate within bore (412) of outer sheath (410) through the rotation of driver (442). In other words, inner needle (430) and driver (442) are translatably coupled at engagement mechanism (445), but rotatably decoupled such that rotation and translation of driver (442) will only translate inner needle (430) without rotating inner needle (430). To this end, housing (414) includes an internal threaded portion (420) and a slot (422) to allow inner needle (430) to slidably translate within bore (412).

Internal threaded portion (420) is configured to engage external threaded portion (443) of driver (442) such that the rotation of driver (442) in a clockwise direction, when viewed from the proximal end, translates inner needle (430) in a distal direction. Conversely, a counter rotation of driver (442) in the counterclockwise direction, when viewed from the proximal end, translates inner needle (430) in a proximal direction. As further seen in FIG. 12, slot (422) extends inwardly into housing (414) and has a longitudinal length parallel to a longitudinal axis (429) of inner needle (430). Inner needle (430) further comprises a latch (444) protruding laterally from shaft (440) along a portion of inner needle (430) contained within housing (414). Latch (444) is configured to engage slot (422), which is configured to inhibit rotation of inner needle (430) as well as constrain the longitudinal translation inner needle (430) to the longitudinal length of slot (422).

Figure 13A:
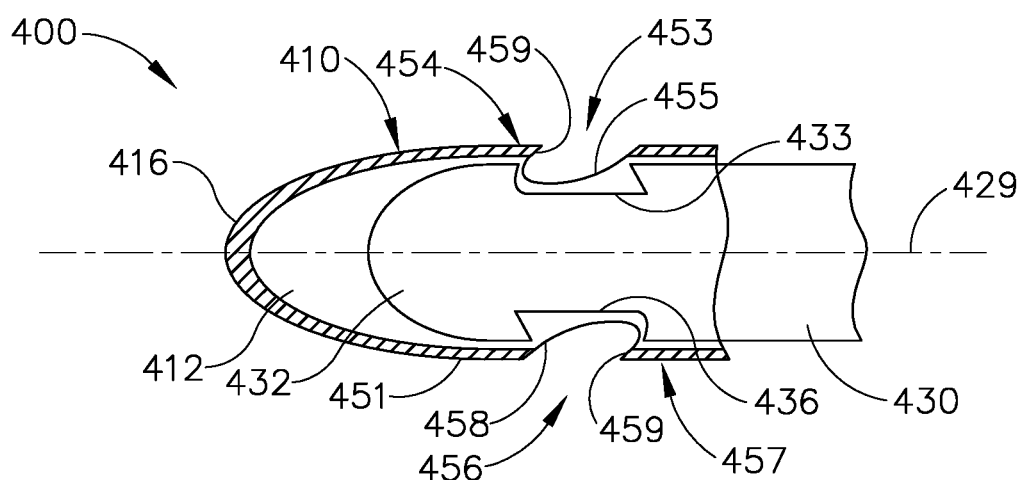
FIG. 13A depicts an enlarged cross-sectional side view of the needle head of FIG. 12 taken along a centerline thereof with the needle head in a retracted position.
Figure 13B:
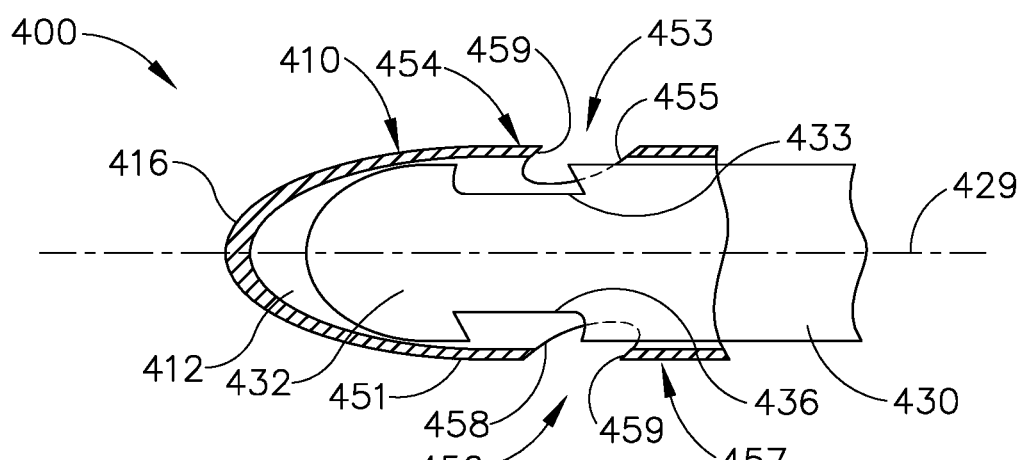
FIG. 13B depicts the enlarged cross-sectional side view of the needle head similar to FIG. 13A, but with the needle head in an extended position.
Figure 13C:
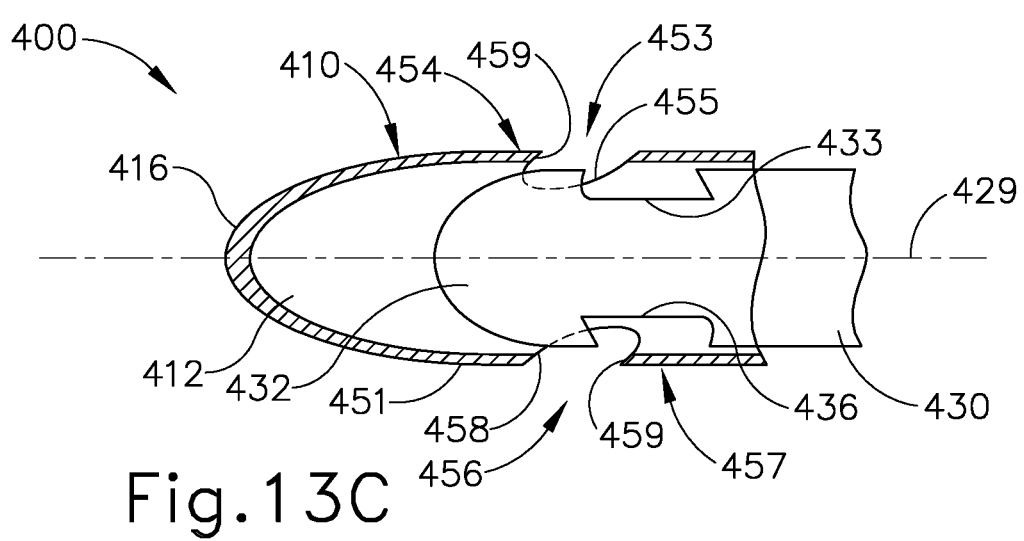
FIG. 13C depicts the enlarged cross-sectional side view of the needle head similar to FIG. 13B, but with the needle head in a third position.

As best seen in FIGS. 13A-13C, outer sheath (410) further includes an upper aperture (453) and a lower aperture (456) proximal to end (416). Apertures (453, 456) are configured to provide communication between an outer radial surface (451) of outer sheath (410) and bore (412) such that apertures (453, 456) expose needle head (432) when inner needle (430) is slidably inserted within bore (412). In particular, upper aperture (453) is positioned along outer sheath (410) to correspond with upper notch (433) on needle head (432) and lower aperture (456) is positioned along outer sheath (410) to correspond with lower notch (436). Apertures (453, 456) extend through outer sheath (410) and comprise catch undercuts (454, 457) and release cam surfaces (455, 458). Catch undercuts (454, 457) have a hooked surface (459) and are configured to receive and hold suture thread (60) (see FIG. 14A) radially inwardly toward outer sheath (410) when suture passer (400) is selectively maneuvered in a catch direction to catch suture thread (60).

Release cam surfaces (455, 458) are positioned respectively between catch undercuts (454, 457) and outer radial surface (451) of outer sheath (410). Release cam surfaces (455, 458) extend distally and radially outwardly from the hooked surfaces (459) of catch undercuts (454, 457) until becoming flush with outer radial surface (451) of outer sheath (410). Release cam surfaces (455, 458) are configured to urge suture thread (60) radially outwardly from catch undercuts (454, 457) to thereby remove suture thread (60) from notches (433, 436) when suture passer (400) is selectively maneuvered in a release direction to release suture thread (60).

Upper aperture (453) is positioned along outer sheath (410) angularly opposite of lower aperture (456) about a longitudinal axis (429) of outer sheath (410). Upper catch undercut (454) is distally oriented on outer sheath (410) relative to upper release cam surface (455) such that upper catch undercut (454) is positioned proximal to distal end (416) and upper release cam surface (455) is positioned distal to distal end (416). In contrast, lower catch undercut (457) is proximally oriented on outer sheath (410) relative to lower release cam surface (458) such that lower catch undercut (457) is positioned distal to distal end (416) and lower release cam surface (458) is positioned proximal to distal end (416).

In the present example, suture passer (400) transitions to a series of positions when a clinician rotates driver (442). In particular, rotation of driver (442) slidably advances inner needle (430) within bore (412) through the threaded engagement of internal threaded portion (420) and external threaded portion (443) to the extent until latch (444) encounters the confined limits of slot (422). As seen in FIG. 13A, driver (442) is rotated until notches (433, 436) are substantially aligned with apertures (453, 456). FIG. 13B shows inner needle (430) in a distally translated position with notches (433, 436) not substantially aligned with apertures (453, 456) but instead substantially covered by bore (412) in a position proximal to distal end (416). Lastly, as seen in FIG. 13C, driver (442) is oppositely rotated until inner needle (430) is in a proximally translated position with notches (433, 436) not substantially aligned with apertures (453, 456) but instead substantially covered by bore (412) in a position distal to distal end (416).

Figure 14A:
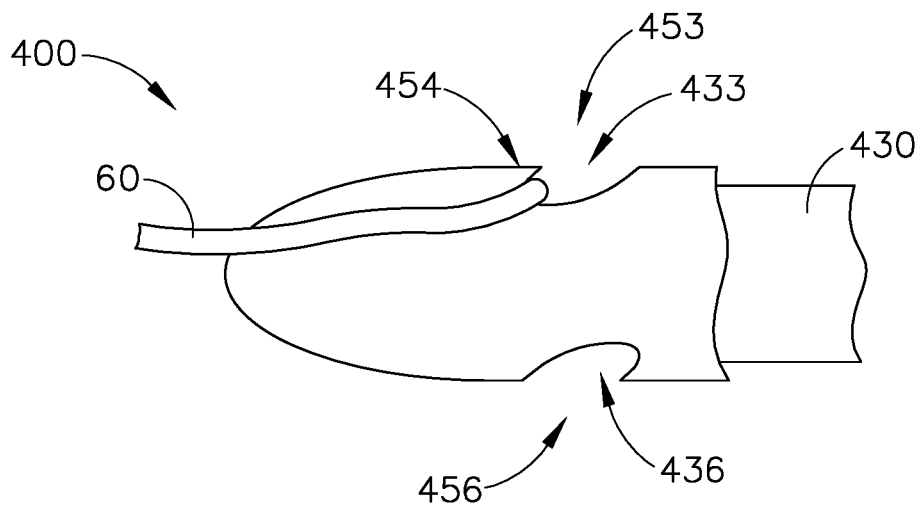
FIG. 14A depicts an enlarged side elevational view of the needle head of FIG. 13A with the needle head in the retracted position and grasping a suture thread within a suture notch.
Figure 14B:
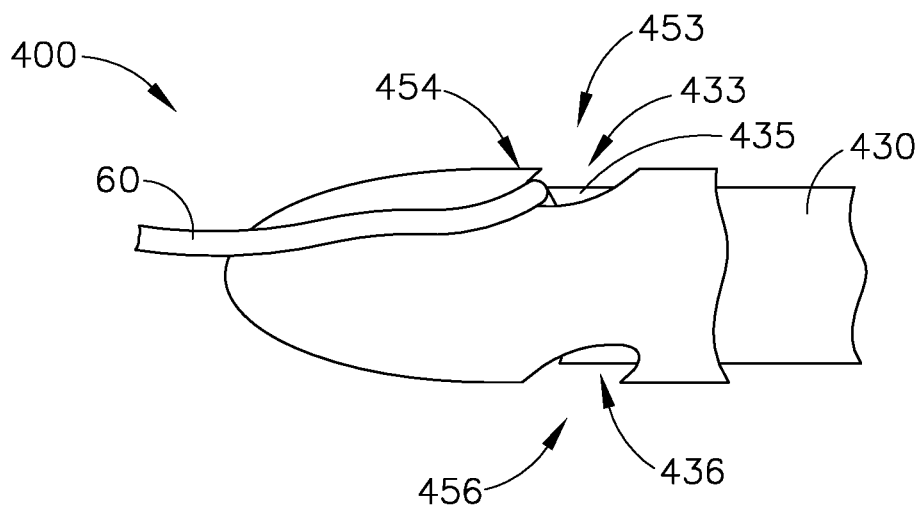
FIG. 14B depicts an enlarged side elevational view of the needle head of FIG. 13B with the needle head in the extended position and securing the suture thread within the suture notch.
Figure 14C:
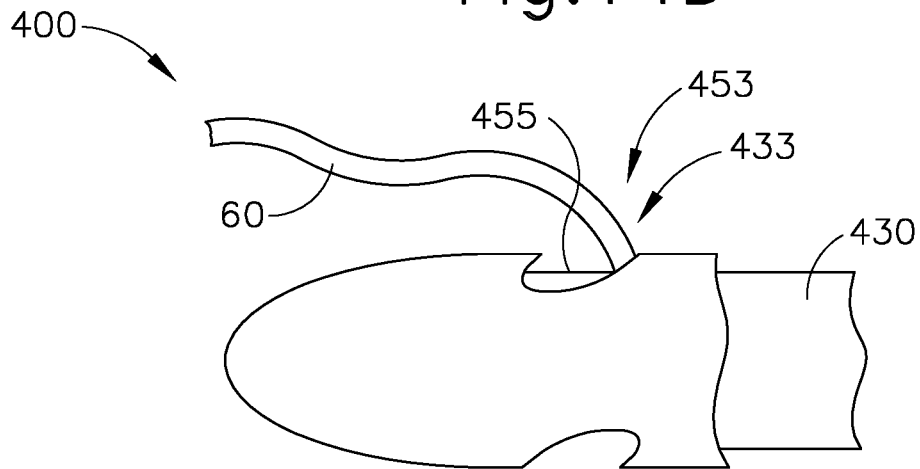
FIG. 14C depicts an enlarged side elevational view of the needle head of FIG. 13C with the needle head returned to the retracted position and releasing the suture thread from within the suture notch.

FIGS. 14A-14C illustrate suture passer (400) capturing and releasing suture thread (60) within upper aperture (453) and upper notch (433). In particular, FIG. 14A depicts notches (433, 436) substantially aligned with apertures (453, 456) (in the position previously illustrated in FIG. 13A) and suture thread (60) releasably secured at upper catch undercut (454) of upper aperture (453). By rotating driver (442), inner needle (430) translates distally within bore (412) of outer sheath (410) thus causing notches (433, 436) to distally translate. In this instance, as seen in FIG. 14B, upper hooked surface (435) of upper notch (433) securely captures suture thread (60) against upper catch undercut (454), thereby preventing suture thread (60) from slipping out from the grasp of suture passer (400). The clinician may then selectively maneuver suture passer (400), with suture thread (60) securely seized, to a preferred position for placement. By rotating driver (442) in a direction opposite of that represented in FIG. 14B, upper notch (433) translates proximally and simultaneously releases suture thread (60) from upper catch undercut (454), as seen in FIG. 14C. As upper notch (433) translates proximally, upper curved surface (434) directs suture thread (60) proximally along upper release cam surface (455) until suture thread (60) is freely released from upper aperture (453).

Figure 15A:
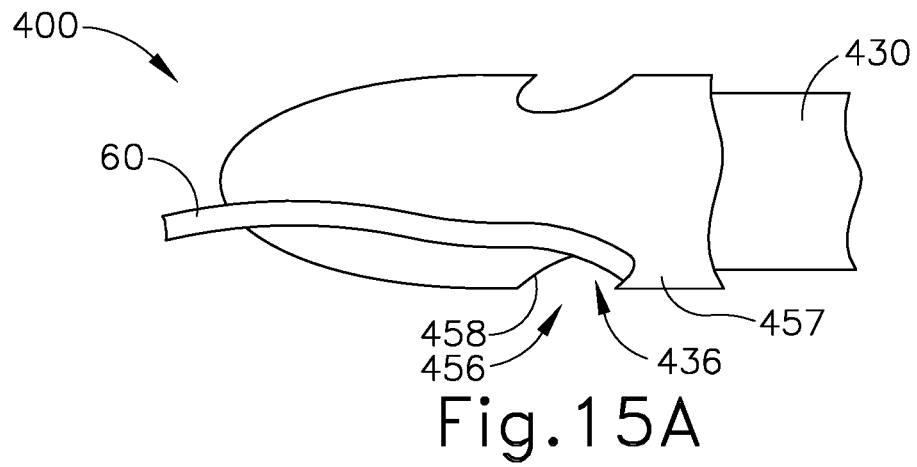
FIG. 15A depicts an enlarged side elevational view of the needle head of FIG. 13A with the needle head in the retracted position and grasping the suture thread within another suture notch.
Figure 15B:
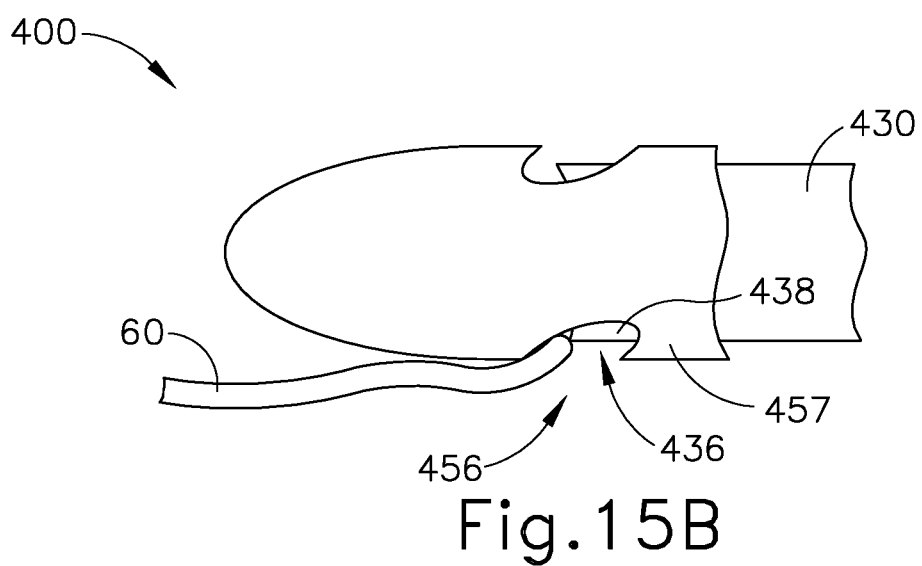
FIG. 15B depicts an enlarged side elevational view of the needle head of FIG. 13B with the needle head in the extended position and releasing the suture thread from within the other suture notch.
Figure 15C:
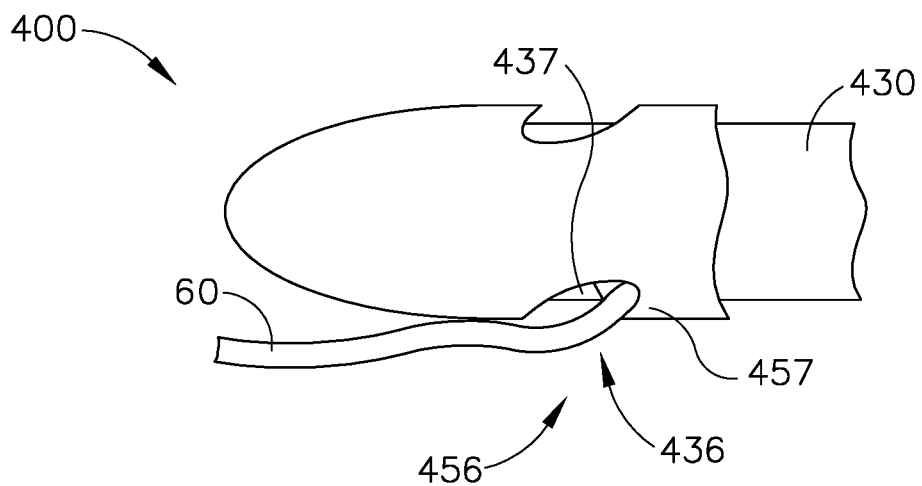
FIG. 15C depicts an enlarged side elevational view of the needle head of FIG. 13C with the needle head returned to the retracted position and securing the suture thread within the other suture notch.

As seen in FIGS. 15A-15C, suture passer (400) may similarly capture and release suture thread (60) within lower aperture (456) and lower notch (436). However, due to the opposite orientation of lower aperture (456), and particularly lower catch undercut (457) and lower release cam surface (458), the identical rotations of driver (442) may generate different interactions between suture passer (400) and suture thread (60). For instance, by rotating driver (442) in a direction like that represented in FIG. 14B, lower curved surface (438) serves to release suture thread (60) from lower catch undercut (457), as seen in FIG. 15B. Thus, the identical rotation of driver (442) generates an opposite interaction between suture thread (60) and upper notch (433) or lower notch (436). In this instance, lower curved surface (438) directs suture thread (60) distally along lower release cam surface (458) until suture thread (60) is freely released from lower aperture (456). Furthermore, by rotating driver (442) in the direction represented in FIG. 14C, wherein lower notch (436) translates in the proximal direction, upper hooked surface (437) securely captures suture thread (60) against upper catch undercut (457), as seen in FIG. 15C.

III. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A suture passer, comprising: (a) a needle extending longitudinally and configured to be manipulated between a catch position and a release position; (b) a first suture notch extending through the needle, wherein the first suture notch includes a first catch undercut configured to receive a suture thread therein and releasably capture the suture thread radially inwardly as the needle is manipulated toward a catch direction; and (c) a second suture notch extending through the needle, wherein the second suture notch includes a second catch undercut configured to receive the suture thread therein and releasably capture the suture thread radially inwardly as the needle is manipulated toward the catch direction.

Example 2

The suture passer of Example 1, wherein the first suture notch further includes a first release cam surface configured to urge the suture thread radially outwardly from the first catch undercut as the needle is manipulated toward a release direction.

Example 3

The suture passer of Example 2, wherein the needle further includes an outer radial surface and the first release cam surface projects between the first catch undercut and the outer radial surface of the needle.

Example 4

The suture passer of Example 3, wherein the first catch undercut defines a hooked surface within the first suture notch, wherein the first release cam surface extends continuously from the hooked surface to the outer radial surface of the needle.

Example 5

The suture passer of Example 4, wherein the first release cam surface extends distally and radially outwardly from the hooked surface to the outer radial surface of the needle.

Example 6

The suture passer of any one or more of Examples 1 through 5, further comprising a sheath having a longitudinal bore extending therethrough, wherein the longitudinal bore slidably receives the needle therein such that the needle is configured to move distally within the longitudinal bore relative to the sheath from a retracted position to an extended position.

Example 7

The suture passer of Example 6, wherein the sheath includes a radial wall extending distally to a distal sheath end, wherein the radial wall includes a first aperture in communication with the longitudinal bore, and wherein the first aperture is configured to longitudinally align with first suture notch and thereby expose the first suture notch for capturing the suture thread through the first aperture.

Example 8

The suture passer of Example 7, wherein the distal sheath end is configured to pierce a tissue.

Example 9

The suture passer of any one or more of Examples 1 through 8, further comprising a driver operatively connected to the needle and configured to selectively translate the needle longitudinally from the retracted position to the extended position.

Example 10

The suture passer of Example 9, wherein the driver is further configured to selectively rotate the needle from the retracted position to the extended position.

Example 11

The suture passer of any one or more of Examples 9 through 10, wherein the driver further includes a resilient member configured to bias the needle toward the retracted position.

Example 12

The suture passer of any one or more of Examples 1 through Example 11, wherein the second suture notch includes a second release cam surface configured to urge the suture thread radially outwardly from the second catch undercut as the needle is manipulated toward the release direction, wherein the needle extends along a longitudinal axis, and wherein first suture notch is positioned angularly opposite from the second suture notch about the longitudinal axis.

Example 13

The suture passer of any one or more of Example 12, further comprising a third suture notch extending through the needle, wherein the third suture notch includes a third catch undercut configured to receive the suture thread therein and releasably capture the suture thread radially inwardly as the needle is manipulated toward the catch direction.

Example 14

The suture passer of Example 13, wherein the third suture notch includes a third release cam surface configured to urge the suture thread radially outwardly from the third catch undercut as the needle is manipulated toward the release direction, wherein the needle extends along a longitudinal axis, and wherein first, second, and third suture notches are longitudinally and angularly positioned about the longitudinal axis in a helical arrangement.

Example 15

The suture passer of any one or more of Examples 1 through 14, wherein the distal needle end has a domed end extending distally therefrom.

Example 16

A suture passer, comprising: (a) a needle extending longitudinally along a longitudinal axis and configured to be manipulated between a catch position and a release position; (b) a first suture notch extending through the needle in a first position about the longitudinal axis, wherein the first suture notch includes: (i) a first catch portion configured to receive a suture thread therein and releasably capture the suture thread as the needle is manipulated toward the catch direction, and (ii) a first release portion configured to urge the suture thread from the first catch portion as the needle is manipulated toward the release direction; and (c) a second suture notch extending through the needle in a second position about the longitudinal axis, wherein the second suture notch includes: (i) a second catch portion configured to receive a suture thread therein and releasably capture the suture thread as the needle is manipulated toward the catch direction, and (ii) a second release portion configured to urge the suture thread from the second catch portion as the needle is manipulated toward the release direction, wherein the first position of the first suture notch is different than the second position of the second suture notch.

Example 17

The suture passer of Example 16, wherein first suture notch is positioned angularly opposite from the second suture notch about the longitudinal axis.

Example 18

The suture passer of any one or more of Examples 16 through 17, further comprising a third suture notch extending through the needle in a third position about the longitudinal axis, wherein the third suture notch includes: (i) a third catch portion configured to receive a suture thread therein and releasably capture the suture thread as the needle is manipulated toward the catch direction, and (ii) a third release portion configured to urge the suture thread from the third catch portion as the needle is manipulated toward the release direction, wherein the third position of the third suture notch is different than the first and second positions of the first and second suture notches, respectively.

Example 19

The suture passer of Example 18, wherein first, second, and third suture notches are longitudinally and angularly positioned in the first, second, and third positions about the longitudinal axis in a helical arrangement.

Example 20

A method of grasping a suture thread within a patient with a suture passer having a needle and a suture notch extending through the needle, wherein the suture notch includes a catch portion and a release portion, wherein the catch portion is configured to receive the suture thread therein and releasably capture the suture thread, and wherein the release portion is configured to urge the suture thread from the catch portion, the method comprising: (a) manipulating the needle from a catch position toward a release position; (b) urging the suture thread with the cam surface from the catch portion of the suture notch; and (c) releasing the suture thread from the catch portion of the suture notch.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

The teachings presented herein may be further combined with various teachings of any one or more of the following: U.S. application Ser. No. 15/637,690, entitled "Needle Guide Instrument with Transverse Suture Capture Feature," filed on Jun. 29, 2017, published as U.S. Pub. No. 2019/0000443 on Jan. 3, 2019, the disclosure of which is incorporated by reference herein; U.S. application Ser. No. 15/637,683, entitled "Trocar with Oblique Needle Insertion Port and Perpendicular Seal Latch," filed on Jun. 29, 2017, published as U.S. Pub. No. 2019/0000505 on Jan. 3, 2019, the disclosure of which is incorporated by reference herein; U.S. application Ser. No. 15/637,688, entitled "Trocar with Oblique Needle Insertion Port and Coplanar Stopcock," filed on Jun. 29, 2017, issued as U.S. Pat. No. 10,485,580 on Nov. 26, 2019, the disclosure of which is incorporated by reference herein; U.S. application Ser. No. 15/637,712, entitled "Suture Passing Instrument with Puncture Site Identification Feature," filed on Jun. 29, 2017, published as U.S. Pub. No. 2019/0000444 on Jan. 3, 2019, the disclosure of which is incorporated by reference herein; U.S. App. Ser. No. 15/637,696, entitled "Trocar Obturator with Transverse Needle Ports," filed on Jun. 29, 2017, published as U.S. Pub. No. 2019/0000506 on Jan. 3, 2019, the disclosure of which is incorporated by reference herein; U.S. application Ser. No. 15/637,707, entitled "Surgical Port with Wound Closure Channels," filed on Jun. 29, 2017, issued as U.S. Pat. No. 10,568,619 on Feb. 25, 2020, the disclosure of which is incorporated by reference herein; U.S. application Ser. No. 15/637,735, entitled "Trocar Obturator with Detachable Rotary Tissue Fastener," filed on Jun. 29, 2017, published as U.S. Pub. No. 2019/0000502 on Jan. 3, 2019, the disclosure of which is incorporated by reference herein; U.S. App. Ser. No. 15/637,778, entitled "Method of Suturing a Trocar Path Incision," filed on Jun. 29, 2017, published as U.S. Pub. No. 2019/0000496 on Jan. 3, 2019, the disclosure of which is incorporated by reference herein; and/or other patents and patent application publications incorporated by reference above.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A suture passer, comprising:
    (a) a needle extending longitudinally and configured to be manipulated between a catch position and a release position;
    (b) a first suture notch extending through the needle, wherein the first suture notch includes a first catch undercut configured to receive a suture thread therein and releasably capture the suture thread radially inwardly as the needle is manipulated toward a catch direction;
    (c) a second suture notch extending through the needle, wherein the second suture notch includes a second catch undercut configured to receive the suture thread therein and releasably capture the suture thread radially inwardly as the needle is manipulated toward the catch direction;
    (d) an unsharpened needle tip disposed at a distal end of the needle, wherein the unsharpened needle tip is configured to inhibit damage to tissue when inserting the suture passer into a patient; and
    (e) a sheath having a longitudinal bore extending at least partially therethrough, wherein the longitudinal bore is configured to slidably receive the unsharpened needle tip of the needle therein, wherein the sheath includes a closed distal end, wherein the sheath is configured to allow the first and second suture notches to releasably capture the suture thread.

2. The suture passer of claim 1, wherein the first suture notch further includes a first release cam surface configured to urge the suture thread radially outwardly from the first catch undercut as the needle is manipulated toward a release direction.

3. The suture passer of claim 2, wherein the needle further includes an outer radial surface and the first release cam surface projects between the first catch undercut and the outer radial surface of the needle.

4. The suture passer of claim 3, wherein the first catch undercut defines a hooked surface within the first suture notch, wherein the first release cam surface extends continuously from the hooked surface to the outer radial surface of the needle.

5. The suture passer of claim 4, wherein the first release cam surface extends distally and radially outwardly from the hooked surface to the outer radial surface of the needle.

6. The suture passer of claim 1, wherein the distal sheath end is configured to pierce the tissue.

7. The suture passer of claim 1, further comprising a driver operatively connected to the needle and configured to selectively translate the needle longitudinally from the retracted position to the extended position.

8. The suture passer of claim 7, wherein the driver is further configured to selectively rotate the needle from the retracted position to the extended position.

9. The suture passer of claim 1, wherein the second suture notch includes a second release cam surface configured to urge the suture thread radially outwardly from the second catch undercut as the needle is manipulated toward the release direction, wherein the needle extends along a longitudinal axis, and wherein first suture notch is positioned angularly opposite from the second suture notch about the longitudinal axis.

10. The suture passer of claim 9, further comprising a third suture notch extending through the needle, wherein the third suture notch includes a third catch undercut configured to receive the suture thread therein and releasably capture the suture thread radially inwardly as the needle is manipulated toward the catch direction.

11. The suture passer of claim 10, wherein the third suture notch includes a third release cam surface configured to urge the suture thread radially outwardly from the third catch undercut as the needle is manipulated toward the release direction, wherein the needle extends along a longitudinal axis, and wherein the first, second, and third suture notches are longitudinally and angularly positioned about the longitudinal axis in a helical arrangement.

12. The suture passer of claim 1, wherein the distal tip is a domed end.

13. The suture passer of claim 1, wherein the sheath includes first and second apertures, wherein the first aperture is configured to selectively align with the first suture notch, wherein the second aperture is configured to selectively align with the second suture notch.

14. The suture passer of claim 1, wherein the first suture notch extends through the needle at a first angular position about a longitudinal axis of the needle, wherein the second suture notch extends through the needle at a second angular position about the longitudinal axis, wherein the second angular position of the second suture notch is angularly opposite from the first angular position of the first suture notch.

15. The suture passer of claim 14, further comprising a third suture notch extending through the needle at the first angular position and proximally spaced from the first suture notch about the longitudinal axis.

16. A suture passer, comprising:
    (a) a needle extending longitudinally along a longitudinal axis and configured to be manipulated between a catch position and a release position;
    (b) a first suture notch extending through the needle at a first angular position about the longitudinal axis, wherein the first suture notch includes:
        (i) a first catch portion configured to receive a suture thread therein and releasably capture the suture thread as the needle is manipulated toward the catch direction, and
        (ii) a first release portion configured to urge the suture thread from the first catch portion as the needle is manipulated toward the release direction;
    (c) a second suture notch extending through the needle at a second angular position about the longitudinal axis, wherein the second angular position of the second suture notch is angularly opposite from the first angular position of the first suture notch, wherein the second suture notch includes:
        (i) a second catch portion configured to receive a suture thread therein and releasably capture the suture thread as the needle is manipulated toward the catch direction, and
        (ii) a second release portion configured to urge the suture thread from the second catch portion as the needle is manipulated toward the release direction; and
    (d) a third suture notch extending through the needle at the first angular position and proximally spaced from the first suture notch about the longitudinal axis, wherein the third suture notch includes:

(i) a third catch portion configured to receive a suture thread therein and releasably capture the suture thread as the needle is manipulated toward the catch direction, and (ii) a third release portion configured to urge the suture thread from the third catch portion as the needle is manipulated toward the release direction.

17. The suture passer of claim 16, wherein the second angular position of the second suture notch is disposed 180 degrees angularly opposite from the first angular position of the first suture notch.

18. The suture passer of claim 16, further comprising a fourth suture notch extending through the needle at the second angular position and longitudinally spaced from the second suture notch about the longitudinal axis, wherein the fourth suture notch includes:

(i) a fourth catch portion configured to receive a suture thread therein and releasably capture the suture thread as the needle is manipulated toward the catch direction, and (ii) a fourth release portion configured to urge the suture thread from the fourth catch portion as the needle is manipulated toward the release direction.

19. A suture passer, comprising:

(a) a needle extending longitudinally and configured to be manipulated between a catch position and a release position, wherein the needle comprises:
  (i) a first suture notch extending through the needle, and
  (ii) a second suture notch extending through the needle, wherein the second suture notch is separate from the first suture notch; and (b) a sheath comprising:
  (i) a longitudinal bore extending longitudinally through the sheath, wherein the longitudinal bore is configured to slidably receive the needle therein,
  (ii) a first aperture configured to align with the first suture notch in the catch position, wherein the first aperture includes a first catch undercut configured to receive a suture thread therein and releasably capture the suture thread radially inwardly as the needle is manipulated toward a catch direction, and
  (iii) a second aperture configured to align with the second suture notch in the catch position, wherein the second aperture includes a second catch undercut configured to receive the suture thread therein and releasably capture the suture thread radially inwardly as the needle is manipulated toward the catch direction.

20. The suture passer of claim 19, wherein the sheath includes a closed distal end.

* * * * *